US012691158B2

(12) United States Patent
Isaacs et al.

(10) Patent No.: US 12,691,158 B2
(45) Date of Patent: Jul. 28, 2026

(54) ALBUMIN-PROAEROLYSIN PRODRUGS

(71) Applicant: THE JOHNS HOPKINS UNIVERSITY, Baltimore, MD (US)

(72) Inventors: John T. Isaacs, Phoenix, MD (US); Samuel R. Denmeade, Ellicott City, MD (US); W. Nathaniel Brennen, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1242 days.

(21) Appl. No.: 17/203,469

(22) Filed: Mar. 16, 2021

(65) Prior Publication Data

US 2021/0205408 A1     Jul. 8, 2021

Related U.S. Application Data

(63) Continuation of application No. 16/815,746, filed on Mar. 11, 2020, now Pat. No. 10,967,046, which is a continuation of application No. 15/544,146, filed as application No. PCT/US2016/013516 on Jan. 15, 2016, now Pat. No. 10,596,226.

(60) Provisional application No. 62/104,275, filed on Jan. 16, 2015.

(51) Int. Cl.
| | |
|---|---|
| *A61K 38/16* | (2006.01) |
| *A61K 35/16* | (2015.01) |
| *A61K 38/38* | (2006.01) |
| *A61K 47/64* | (2017.01) |
| *A61K 47/65* | (2017.01) |
| *C07K 14/47* | (2006.01) |
| *C07K 14/765* | (2006.01) |
| *C07K 19/00* | (2006.01) |

(52) U.S. Cl.
CPC ............ *A61K 38/164* (2013.01); *A61K 35/16* (2013.01); *A61K 38/385* (2013.01); *A61K 47/643* (2017.08); *A61K 47/65* (2017.08); *C07K 14/4748* (2013.01); *C07K 14/765* (2013.01); *C07K 19/00* (2013.01); *C07K 2319/21* (2013.01)

(58) Field of Classification Search
CPC .... A61K 38/164; A61K 47/643; A61K 47/65; A61K 35/385; C07K 14/4748; C07K 14/765; C07K 19/00; C07K 2319/21
See application file for complete search history.

(56) References Cited

U.S. PATENT DOCUMENTS 6,946,134 B1 * 9/2005 Rosen .................. C07K 14/765
435/7.1

FOREIGN PATENT DOCUMENTS

| WO | 2005042034 A1 | 5/2005 |
|---|---|---|
| WO | 2012054929 A2 | 4/2012 |

OTHER PUBLICATIONS

Denmeade, S., et al., "Concentration of enzymatically active prostate-specific antigen (PSA) in the extracellular fluid of primary human prostate cancers and human prostatic cancer xenograft models" Prostate (2001) vol. 48 pp. 1-6.
Denmeade, S., et al., "Phase 1and 2 studies demonstrate the safety of intraprostatic injection of PXR302 for the targeted treatment of lower urinary tract symptoms secondary to benign prostatic hyperplasia" Eur Urol (2011) vol. 59, pp. 747-754.
Denmeade, S., et al., "Engineering enzymatically activated "molecular grenades" for cancer" Oncotarget (2012) vol. 3, pp. 666-667.
Denmeade, S., et al., "Engineering a Prostate-specific Membrane Antigen-Activated Tumor Endothelial Cell Prodrug for Cancer Therapy" Sci Trans Med (2012) vol. 4: 140ra86.
Kratz, F, "Albumin as a drug carrier: design of prodrugs, drug conjugates, and nanoparticles" J Controlled Release (2008) vol. 132, pp. 171-183.
Osusky, M., et al., "A chimera of interleukin 2 binding variant of aerolysin is selectively toxic to cells displaying the interleukin 2 receptor" J Biol Chem (2008) vol. 283, pp. 1572-1579.
Williams, S., et al., A prostate-specific antigen-activated channel-forming toxin as therapy for prostatic disease. J Natl Cancer Inst. (2007) vol. 99, pp. 376-385.
Zhao, H., et al., "Increasing the homogeneity, stability and activity of human serum albumin and interferon-a2b fusion protein by linker engineering", Protein Expression and Purification, (2008) vol. 61, pp. 73-77.

* cited by examiner

*Primary Examiner* — Robert A Zeman
(74) *Attorney, Agent, or Firm* — Casimir Jones, S.C.; Kelly A. Barton

(57) ABSTRACT

The present invention relates to the field of cancer. More specifically, the present invention provides compositions and methods for treating cancer using albumin-proaerolysin prodrugs. Accordingly, in one aspect, the present invention provides prodrug compositions. In certain embodiments, a prodrug composition comprises a prostate-specific antigen (PSA)-activated pro-aerolysin (PA), wherein a PSA cleavable linker replaces the native furin cleavage site within PA; and human serum albumin (HSA) or a fragment thereof fused to the N-terminus of the PSA-activated PA.

10 Claims, No Drawings

Specification includes a Sequence Listing.

ALBUMIN-PROAEROLYSIN PRODRUGS

CROSS-REFERENCE TO RELATED APPLICATIONS

This application is a Continuation of U.S. patent application Ser. No. 16/815,746, filed Mar. 11, 2020, which is a Continuation of U.S. patent application Ser. No. 15/544,146, filed Jul. 17, 2017, now U.S. Pat. No. 10,596,226, granted Mar. 24, 2020, which is a 35 U.S.C. § 371 U.S. national entry of International Application PCT/US2016/013516, having an international filing date of Jan. 15, 2016, which claims the benefit of U.S. Provisional Application No. 62/104,275, filed Jan. 16, 2015, the content of each of the aforementioned applications is herein incorporated by reference in their entirety.

STATEMENT OF GOVERNMENTAL INTEREST

This invention was made with government support under grant no. CA058236, awarded by the National Institutes of Health. The government has certain rights in the invention.

FIELD OF THE INVENTION

The present invention relates to the field of cancer. More specifically, the present invention provides compositions and methods for treating cancer using albumin-proaerolysin prodrugs.

INCORPORATION-BY-REFERENCE OF MATERIAL SUBMITTED ELECTRONICALLY

This application contains a sequence listing. It has been submitted electronically via EFS-Web as an ASCII text file entitled "P12343-02_ST25.txt." The sequence listing is 61,919 bytes in size, and was created on Jan. 14, 2016. It is hereby incorporated by reference in its entirety.

BACKGROUND OF THE INVENTION

Following systemic delivery, an effective drug for a metastatic prostate cancer patient must selectively kill malignant cells without producing unacceptable off-target side effects (i.e., unacceptable levels of killing or injuring normal cells in host tissue). This is a daunting engineering challenge. Based upon the fact that cancer cells often acquire addiction to specific oncogenic signaling pathways, a new approach has emerged focused upon designing drugs to selectively inhibit only particular oncogenic signaling protein targets. In theory, such highly selective oncogene-based inhibitors target growth suppression and/or death of individual oncogene-addicted cancer cells sparing host normal cells. As a class, these new oncogene-targeted inhibitors are less toxic than chemotherapeutics, but they are not without side effects. More significantly, their therapeutic efficacy is limited by heterogeneity within the cancer cell population with regards to addiction to the specific oncogenic signaling resulting in drug resistance. Accordingly, new approaches are necessary to overcome tumor cell heterogeneity based therapeutic resistance.

SUMMARY OF THE INVENTION

The present invention is based, at least in part, on the development of a fusion protein in which albumin is fused to a variant proaerolysin prodrug. In a specific embodiment of the prodrug composition, the C-terminus of Human Serum albumin (HSA) is fused via a Prostate Specific Antigen (PSA) cleavable peptide linker (e.g., HSSKLQ, SEQ ID NO: 2) to the N-terminus of PSA-proaerolysin to generate a novel recombinant fusion protein which will not bind to GPI-anchored proteins on normal cells in the blood or host tissues. Instead, it will accumulate via an enhanced permeability and retention (EPR) effect within sites of metastatic prostate cancer where enzymatically active PSA in the extracellular fluid will hydrolyze the HSA linker liberating PSA-proaerolysin. Additionally, PSA will also remove the C-terminal inhibitory peptide from PSA-proaerolysin to generate aerolysin monomers which can oligomerize to form the heptameric pores that will result in selective killing of cells only in the site of metastatic prostate cancer.

Accordingly, in one aspect, the present invention provides prodrug compositions. In certain embodiments, a prodrug composition comprises a prostate-specific antigen (PSA)-activated pro-aerolysin (PA), wherein a PSA cleavable linker replaces the native furin cleavage site within PA; and human serum albumin (HSA) or a fragment thereof fused to the N-terminus of the PSA-activated PA. In one embodiment, the PSA cleavable linker comprises SEQ ID NO: 5. In another embodiment, the PSA cleavable linker replaces the amino acids at position 427-432 of SEQ ID NO: 2. In yet another embodiment, the HSA or fragment thereof comprises the C-terminal end of HSA. In a specific embodiment, the HSA or fragment thereof comprises SEQ ID NO: 27.

In yet another specific embodiment, the HSA or fragment thereof is fused to the N-terminus of the PSA-activated PA with at least one PSA-cleavable linker sequence. In a particular embodiment, the at least one PSA-cleavable linker sequence comprises SEQ ID NO: 5. The at least one PSA-cleavable linker sequence can be a series of identical linker sequences or a combination of sequences and includes at least 1, 2, 3, 4, 5, 6, 7, 8, 9, 10 or more linker sequences. In a more particular embodiment, the HSA or fragment thereof is fused to the N-terminus of the PSA-activated PA with four identical PSA-cleavable linker sequences, wherein the linker sequence comprises SEQ ID NO: 5.

The present invention also provides a recombinant protein comprising SEQ ID NO: 48. In a specific embodiment, the protein further comprises a polyhistidine tag. In a more specific embodiment, the polyhistidine tag comprises six histidines at the C-terminus of SEQ ID NO: 48.

The present invention also provides a prodrug composition comprising a prostate-specific protease-activated pro-aerolysin (PA), wherein a prostate-specific protease cleavable linker replaces the native furin cleavage site within PA; and a blood plasma protein or a fragment thereof fused to the N-terminus of the PSA-activated PA. In one embodiment, the prostate-specific protease comprises PSA, prostate specific membrane antigen (PSMA), or human glandular kallikrein 2 (HK2). In certain embodiments, the blood plasma protein comprises albumin. In a more specific embodiment, the blood plasma protein comprises human serum albumin.

DETAILED DESCRIPTION OF THE INVENTION

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

I. Definitions

Aerolysin; A channel-forming toxin produced as an inactive protoxin called proaerolysin (PA) (wild-type PA is shown in SEQ ID NOS; 1 and 2). The PA protein contains many discrete functionalities that include a binding domain (approximately amino acids 1-83 of SEQ ID NO: 2), a toxin domain (approximately amino acids 84-426 of SEQ ID NO: 2), and a C-terminal inhibitory peptide domain (approximately amino acids 427-470) of SEQ ID NO: 2) that contains a protease activation site (amino acids 427-432 of SEQ ID NO: 2).

The binding domain recognizes and binds to glycophosphatidylinositol (GPI) membrane anchors including those found in Thy-1 on T lymphocytes, the PIGA gene product found in erythrocyte membranes, and Prostate Stem Cell Antigen (PSCA). Most mammalian cells express GPI anchored proteins on their surfaces. The activation or proteolysis site within wildtype PA is a six amino acid sequence that is recognized as a proteolytic substrate by the furin family of proteases. Wild-type PA is activated upon hydrolysis of a C-terminal inhibitory segment by furin. Activated aerolysin binds to GPI-anchored proteins in the cell membrane and forms a heptamer that inserts into the membrane producing well-defined channels of ~17 Å. Channel formation leads to rapid cell death via necrosis. Wild-type aerolysin is toxic to mammalian cells, including erythrocytes, for example at 1 nanomolar or less.

Antibody; Immunoglobulin molecules and immunologically active portions of immunoglobulin molecules, i.e., molecules that contain an antigen binding site which specifically binds (immunoreacts with) an antigen. A naturally occurring antibody (e.g., IgG) includes four polypeptide chains, two heavy (H) chains and two light (L) chains inter-connected by disulfide bonds. However, the antigen-binding function of an antibody can be performed by fragments of a naturally occurring antibody. Thus, these antigen-binding fragments are also intended to be designated by the term antibody. Examples of binding fragments encompassed within the term antibody include (i) an Fab fragment consisting of the VL, VH, CL and CH1 domains; (ii) an Fd fragment consisting of the VH and CHI domains; (iii) an Fv fragment consisting of the VL and VH domains of a single arm of an antibody, (iv) a dAb fragment which consists of a VH domain; (v) an isolated complimentarily determining region (CDR); and (vi) an F (ab) 2 fragment, a bivalent fragment comprising two Fab fragments linked by a disulfide bridge at the hinge region. Furthermore, although the two domains of the Fv fragment are coded for by separate genes, a synthetic linker can be made that enables them to be made as a single protein chain (known as single chain Fv (scFv)) by recombinant methods. Such single chain antibodies are also included. In one embodiment, an antibody includes camelized antibodies.

In one example, antibody fragments are capable of cross-linking their target antigen, e.g., bivalent fragments such as F (ab) 2 fragments. Alternatively, an antibody fragment which does not itself crosslink its target antigen (e.g., a Fab fragment) can be used in conjunction with a secondary antibody which serves to crosslink the antibody fragment, thereby crosslinking the target antigen. Antibodies can be fragmented using conventional techniques and the fragments screened for utility in the same manner as described for whole antibodies. An antibody is further intended to include bispecific and chimeric molecules that specifically bind the target antigen.

Specifically binds; Binding that occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M. As used herein, the terms "specific binding" or "specifically binding" when used in reference to the interaction of an antibody and a protein or peptide means that the interaction is dependent upon the presence of a particular structure (i.e., the epitope) on the protein.

Cancer; Malignant neoplasm that has undergone characteristic anaplasia with loss of differentiation, increase rate of growth, invasion of surrounding tissue, and is capable of metastasis.

cDNA (complementary DNA); A piece of DNA lacking internal, non-coding segments (introns) and regulatory sequences which determine transcription. cDNA can be synthesized in the laboratory by reverse transcription from messenger RNA extracted from cells.

Chemical synthesis; An artificial means by which one can make a protein or peptide. A synthetic protein or peptide is one made by such artificial means.

Chemotherapy; In cancer treatment, chemotherapy refers to the administration of one or a combination of compounds to kill or slow the reproduction of rapidly multiplying cells. Chemotherapeutic agents include those known by those skilled in the art, including, but not limited to; 5-fluorouracil (5-FU), azathioprine, cyclophosphamide, antimetabolites (such as Fludarabine), antineoplastics (such as Etoposide, Doxorubicin, methotrexate, and Vincristine), carboplatin, cis-platinum and the taxanes, such as taxol and taxotere. Such agents can be co-administered with the disclosed variant PA fusion proteins to a subject. Alternatively or in addition, chemotherapeutic agents can be administered prior to and/or subsequent to administration of the disclosed variant PA fusion proteins to a subject. In one example, chemotherapeutic agents are co-administered with hormonal and radiation therapy, along with the disclosed variant PA fusion proteins, for treatment of a localized prostate carcinoma.

Conservative substitution; One or more amino acid substitutions (for example 1, 2, 3, 4, 5, 6, 7, 8, 9, 10 or more residues) for amino acid residues having similar biochemical properties. Typically, conservative substitutions have little to no impact on the activity of a resulting polypeptide. For example, ideally, a modified PA peptide including one or more conservative substitutions retains proaerolysin activity. A polypeptide can be produced to contain one or more conservative substitutions by manipulating the nucleotide sequence that encodes that polypeptide using, for example, standard procedures such as site-directed mutagenesis or PCR.

Substitutional variants are those in which at least one residue in the amino acid sequence has been removed and a different residue inserted in its place. Examples of amino acids which may be substituted for an original amino acid in a protein and which are regarded as conservative substitutions include; Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Permissive substitutions are non-conservative amino acid substitutions, but also do not significantly alter proaerolysin activity. An example is substitution of Cys for Ala at position 300 of SEQ ID NO: 2 or 4. Further information about conservative substitutions can be found in, among other locations in, Ben-Bassat et al., (J. Bacteria 169:751-7, 1987), O'Regan et al., (Gene 77: 237-51, 1989), Sahin-Toth et al., (Protein Sci. 3: 240-7, 1994), Hochuli et al., (Bio/Technology 6: 1321-5, 1988), WO 00/67796 (Curd et al.) and in standard textbooks of genetics and molecular biology. In one example, such variants can be readily selected for additional testing by performing an assay to determine if the variant retains variant PA fusion protein activity.

Deletion; The removal of a sequence of a nucleic acid, for example DNA, the regions on either side being joined together.

DNA; Deoxyribonucleic acid. DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Enhance; To improve the quality, amount, or strength of something. In one embodiment, a therapy enhances the ability of a subject to reduce tumors, such as a prostate carcinoma, in the subject if the subject is more effective at fighting tumors. In another embodiment, a therapy enhances the ability of an agent to reduce tumors, such as a prostate carcinoma, in a subject if the agent is more effective at reducing tumors. Such enhancement can be measured using the methods disclosed herein, for example determining the decrease in tumor volume.

Functional Deletion; A mutation, partial or complete deletion, insertion, or other variation made to a gene sequence which renders that part of the gene sequence non-functional. For example, functional deletion of a PA binding domain results in a decrease in the ability of PA to bind to and concentrate in the cell membrane. This functional deletion can be reversed by inserting another functional binding domain into proaerolysin, such as a prostate-specific binding domain, for example, an LHRH peptide.

Examples of methods that can be used to functionally delete a proaerolysin binding domain, include, but are not limited to; deletion of about amino acids 1-83 of SEQ ID NO: 2 or fragments thereof, such as about amino acids 45-66 of SEQ ID NO: 2, or inserting one or more of the following mutations into a variant proaerolysin sequence W45A, 147E, M57A, Y61A, K66Q (amino acid numbers refer to SEQ ID NO: 2) (for example, see Mackenzie et al. J. Biol. Chem. 274: 22604-22609, 1999). In another example, functional deletion of a native PA furin cleavage site results in a decrease in the ability of PA to be cleaved and activated by furin, when compared to a wild-type PA molecule.

Immobilized; Bound to a surface, such as a solid surface. A solid surface can be polymeric, such as polystyrene or polypropylene. In one embodiment, the solid surface is in the form of a bead. In another embodiment, the surface includes a modified PA toxin, and in some examples further includes one or more prostate-specific binding ligands, such as LHRH peptide, PSMA antibody, and PSMA single chain antibody. Ideally, the modified PA toxin is liberated from the bead once the bead reaches the prostate cell target. Methods of immobilizing peptides on a solid surface can be found in WO 94/29436, and U.S. Pat. No. 5,858,358. Examples of how the molecules can be attached to the bead include, but are not limited to; HSA-PSA cleavage site/linker-PA-bead-prostate binding ligand; or prostate binding ligand-bead-HSA-cleavage linker-PA.

Isolated; An "isolated" biological component (such as a nucleic acid molecule or protein) has been substantially separated or purified away from other biological components in the cell of the organism in which the component naturally occurs (i.e., other chromosomal and extrachromosomal DNA and RNA). Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins. An isolated cell is one which has been substantially separated or purified away from other biological components of the organism in which the cell naturally occurs.

Malignant; Cells that have the properties of anaplasia invasion and metastasis.

Mammal; This term includes both human and non-human mammals. Similarly, the terms "subject" and "patient" are interchangeable and include both human and veterinary subjects. Examples of mammals include, but are not limited to, humans, pigs, cows, goats, cats, dogs, rabbits and mice.

Neoplasm; Abnormal growth of cells.

Normal Cell; Non-tumor cell, non-malignant, uninfected cell.

Oligonucleotide; A linear polynucleotide sequence of up to about 200 nucleotide bases in length, for example a polynucleotide (such as DNA or RNA) which is at least about 6 nucleotides, for example at least 15, 50, 100 or 200 nucleotides long.

Operably linked; A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

ORF (open reading frame); A series of nucleotide triplets (codons) coding for amino acids without any termination codons. These sequences are usually translatable into a peptide.

Polynucleotide; A linear nucleic acid sequence of any length. Therefore, a polynucleotide includes molecules which are at least 5, 15, 50, 100, 200, 400, 500, 1000, 1100, or 1200 (oligonucleotides) and also nucleotides as long as a full-length cDNA or chromosome.

Proaerolysin; The inactive protoxin of aerolysin. The cDNA and protein of a wild-type or native proaerolysin (PA) are shown in SEQ ID NOS; 1 and 2, respectively. In one example, a variant or modified proaerolysin molecule includes a prostate-specific protease cleavage site, such as a PSA-specific cleavage site, which permits activation of the variant PA in the presence of a prostate-specific protease such as PSA, PMSA, or HK2. In one example, a prostate-specific protease cleavage site is inserted into the native furin cleavage site of PA, such that PA is activated in the presence of a prostate-specific protease, but not furin. Alternatively, the furin cleavage site can be functionally deleted using mutagenesis of the six amino acid sequence, and a prostate-specific protease cleavage sequence can be inserted. In another example, a variant PA molecule further includes deletion or substitution of one or more of the native PA amino acids. In yet another example, a variant PA molecule further includes another molecule (such as an antibody or peptide) linked or added to (or within) the variant PA molecule. In another example, a variant PA molecule includes a prostate-tissue specific binding domain.

In another example, a variant PA molecule further includes a functionally deleted binding domain (about amino acids 1-83 of SEQ ID NO: 2). Functional deletions can be made using any method known in the art, such as deletions, insertions, mutations, or substitutions. Examples include, but are not limited to deleting the entire binding domain (or portions thereof) or introduction of point mutations, which result in a binding domain with decreased function. For example, a PA molecule which has a functionally deleted binding domain (and no binding sequence substituted therefor), will have a decreased ability to accumulate in a cell membrane, and therefore lyse cells at a slower rate than a wild-type PA sequence. Also disclosed are variant PA proteins in which the native binding domain is functionally deleted and replaced with a prostate-tissue specific binding domain as described below;

In another example, a variant or modified PA molecule includes a PSA cleavage site, and a functionally deleted binding domain which is replaced with a prostate-tissue specific binding domain. Such variant PA fusion proteins are targeted to prostate cells via the prostate-tissue specific binding domain, and activated in the presence of PSA.

Particular non-limiting examples of variant PSA proteins are shown in SEQ ID NOS; 4, 7, 10, 13, 24, and 25.

Modified PA activity is the activity of an agent in which the lysis of cells is affected. Cells include, but are not limited to prostate-specific protease secreting cells, such as PSA-secreting cells, such as prostate cancer cells, such as slow-proliferating prostate cancer cells. Agents include, but are not limited to, modified PA proteins, nucleic acids, specific binding agents, including variants, mutants, polymorphisms, fusions, and fragments thereof, disclosed herein. In one example, modified PA activity is said to be enhanced when modified PA proteins or nucleic acids, when contacted with a PSA-secreting cell (such as a prostate cancer cell), promote lysis and death of the cell, for example by at least 10%, or for example by at least 25%, 50%, 100%, 200% or even 500%, when compared to lysis of a non-PSA producing cell. In other examples, modified PA activity is said to be enhanced when modified PA proteins and nucleic acids, when contacted with a tumor, decrease tumor cell volume, such as a prostate tumor, for example by at least 10% for example by at least 20%, 30%, 40%, 50%, 60%, 70%, 75%, 80%, 85%, 90%, 95%, 98%, or even 100% (complete elimination of the tumor). Assays which can be used to determine if an agent has modified PA activity are described, for example, in U.S. Pat. Nos. 7,838,266, 7,745,395, and 7,282,476, which are all incorporated herein by reference.

Promoter; An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription.

Prostate-specific promoter; A promoter responsive to testosterone and other androgens, which therefore promotes gene expression in prostate cells. Examples include, but are not limited to the probasin promoter; the prostate specific antigen (PSA) promoter; the prostate specific membrane antigen (PSMA) promoter; and the human glandular kallikrein 2 (HK2) promoter.

Prostate-specific protease cleavage site; A sequence of amino acids which is recognized and specifically and efficiently hydrolyzed (cleaved) by a prostate-specific protease. Examples include, but are not limited to a PSA-specific cleavage site, a PSMA-specific cleavage site and an HK2-specific cleavage site. Variant PA fusion proteins of the present invention can comprise one or more cleavage sites/linkers. For example, albumin can be fused to the N-terminus of a variant PA protein using one, two, three, four, five, six or more prostate-specific protease cleavage site linkers.

PSA-specific cleavage site; is a sequence of amino acids which is recognized and specifically and efficiently hydrolyzed (cleaved) by prostate specific antigen (PSA). Such peptide sequences can be introduced into other molecules, such as PA, to produce prodrugs that are activated by PSA. Upon activation of the modified PA by PSA, PA is activated and can exert its cytotoxicity. Examples of PSA-specific cleavage sites include, but are not limited to, those shown in SEQ ID NOS; 5, 8 and 14-21, those disclosed in U.S. Pat. Nos. 6,391,305; 6,368,598; 6,265,540; 5,998,362; 5,948, 750; and 5,866,679.

PSMA-specific cleavage site; Particular examples of PSMA-specific cleavage sites can be found in WO/0243773 to Isaacs and Denmeade (herein incorporated by reference). The PSMA cleavage site includes at least the dipeptide, $X_1X_2$. This peptide contains the amino acids Glu or Asp at position $X_1$. $X_2$ can be Glu, Asp, Gln, or Asn. Tripeptides $X_1X_2X_3$ are also suitable, with $X_1$ and $X_2$ defined as before, with $X_3$ as Glu, Asp, Gln or Asn. Tetrapeptides $X_1X_2X_3X_4$ are also suitable, with $X_1$-3 defined as above, and with $X_4$ as Glu, Asp, Gln or Asn. Pentapeptides $X_1X_2X_3X_4X_5$ are also suitable, with $X_{14}$ defined as above, and with $X_5$ as Glu, Asp, Gln or Asn. Hexapeptides $X_1X_2X_3X_4X_5X_6$ are also suitable, with $X_1$-5 defined as above, and with $X_6$ as Glu, Asp, Gln or Asn. Further peptides of longer sequence length can be constructed in similar fashion.

Generally, the peptides are of the following sequence; $X_1 \ldots X_n$, where n is 2 to 30, preferably 2 to 20, more preferably 2 to 15, and even more preferably 2 to 6, where $X_1$ is Glu, Asp, Gln or Asn, but is preferably Glu or Asp, and $X_2$-$X_n$ are independently selected from Glu, Asp, Gln and Asn. Some preferred peptide sequences are as above, except that $X_2$-$X_n$-1 are independently selected from Glu, and Asp, and $X_n$ is independently selected from Glu, Asp, Gln and Asn. The length of the peptide can be optimized to allow for efficient PSMA hydrolysis, enhanced solubility of therapeutic drug in aqueous solution, if this is needed, and limited non-specific cytotoxicity in vitro.

HK2-specific cleavage site; Particular examples of HK2-specific cleavage sites are disclosed in WO01/09165 and U.S. Patent Publication 20120309692 and include, but are not limited to, Lys-Arg-Arg. Ser-Arg-Arg. Ala-Arg-Arg. His-Arg-Arg. Gln-Arg-Arg. Ala-Phe-Arg. Ala-Gln-Arg. Ala-Lys-Arg. Ala-Arg-Lys. Ala-His-Arg. Gln-Lys-Arg-Arg (SEQ ID NO: 28), Lys-Ser-Arg-Arg (SEQ ID NO: 29), Ala-Lys-Arg-Arg (SEQ ID NO: 30), Lys-Lys-Arg-Arg (SEQ ID NO: 31), His-Lys-Arg-Arg (SEQ ID NO: 32), Lys-Ala-Phe-Arg (SEQ ID NO: 33), Lys-Ala-Gln-Arg (SEQ ID NO: 34), Lys-Ala-Lys-Arg (SEQ ID NO: 35), Lys-Ala-Arg-Lys (SEQ ID NO: 36), Lys-Ala-His-Arg (SEQ ID NO: 37), His-Ala-Gln-Lys-Arg-Arg (SEQ ID NO: 38), Gly-Gly-Lys-Ser-Arg-Arg (SEQ ID NO: 39), His-Glu-Gln-Lys-Arg-Arg (SEQ ID NO: 40), His-Glu-Ala-Lys-Arg-Arg (SEQ ID NO: 41), Gly-Gly-Gln-Lys-Arg-Arg (SEQ ID NO: 42), His-Glu-Gln-Lys-Arg-Arg (SEQ ID NO: 43), Gly-Gly-Ala-Lys-Arg-Arg (SEQ ID NO: 44), His-Glu-Gln-Lys-Arg-Arg (SEQ ID NO: 45), Gly-Gly-Lys-Lys-Arg-Arg (SEQ ID NO: 46), and Gly-Gly-His-Lys-Arg-Arg (SEQ ID NO: 47).

PRX302; A modified proaerolysin where the furin site of proaerolysin has been replaced with a PSA-specific cleavage site. SEQ ID NOS; 3 and 4 show the PRX302 cDNA and protein sequence, respectively. SEQ ID NO: 26 shows the protein sequence of SEQ ID NO: 4 with an N-terminal His tag. The term "PRX302" includes the proteins of both SEQ ID NO: 4 and SEQ ID NO: 26.

Prostate tissue-specific binding domain; A molecule, such as a peptide ligand, toxin, or antibody, which has a higher specificity for prostate cells than for other cell types. In one example, a prostate tissue specific binding domain has a lower Ko in prostate tissue or cells than in other cell types. (i.e., binds selectively to prostate tissues as compared to other normal tissues of the subject), for example at least a 10-fold lower $K_D$, such as an at least 20-, 50-, 75-, 100- or even 200-fold lower $K_D$. Such sequences can be used to target an agent, such as a variant PA molecule, to the prostate. Examples include, but are not limited to; antibodies which recognize proteins that are relatively prostate-specific such as PSA, PSMA, HK2, prostasin, and hepsin; ligands which have prostate-selective receptors such as natural and synthetic luteinizing hormone releasing hormone (LHRH); and endothelin (binding to cognate endothelin receptor).

Purified; The term "purified" does not require absolute purity; rather, it is intended as a relative term. Thus, for example, a substantially purified protein or nucleic acid preparation (such as the modified PA toxins disclosed herein) is one in which the protein or nucleic acid referred to is more pure than the protein in its natural environment within a cell or within a production reaction chamber (as appropriate). For example, a preparation of a modified PA protein is purified if the protein represents at least 50%, for example at least 70%, of the total protein content of the preparation. Methods for purification of proteins and nucleic acids are well known in the art. Examples of methods that can be used to purify a protein, such as a modified PA, include, but are not limited to the methods disclosed in Sambrook et al. (Molecular Cloning; A Laboratory Manual, Cold Spring Harbor, N.Y., 1989, Ch. 17).

Recombinant; A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques. A recombinant protein is one that results from expressing a recombinant nucleic acid encoding the protein.

Sample; Biological samples containing genomic DNA, cDNA, RNA, or protein obtained from the cells of a subject, such as those present in peripheral blood, urine, saliva, semen, tissue biopsy, surgical specimen, fine needle aspirates, amniocentesis samples and autopsy material. In one example, a sample includes prostate cancer cells obtained from a subject.

Sequence identity/similarity; The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in; Smith & Waterman, Adv. Appl. Math. 2:482, 1981; Needleman & Wunsch, J. Mol. Biol. 48:443, 1970; Pearson & Lipman, Proc. Natl. Acad. Sci. USA 85: 2444, 1988; Higgins & Sharp, Gene, 73: 237-44, 1988; Higgins & Sharp, CABIOS 5: 151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24: 307-31, 1994. Altschul et al., J. Mol. Biol. 215: 403-10, 1990, presents a detailed consideration of sequence alignment methods and homology calculations.

The NCBI Basic Local Alignment Search Tool (BLAST) (Altschul et al., J. Mol. Biol. 215: 403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least 70%, 75%, 80%, 85%, 86%, 87%, 88%, 89%, 90%, 91%, 92%, 93%, 94%, 95%, 96%, 97%, 98 or even 99% sequence identity. When less than the entire sequence is being compared for sequence identity, homologs will typically possess at least 75% sequence identity over short windows of $10^{-20}$ amino acids, and can possess sequence identities of at least 85%, 86%, 87%, 88%, 89%, 90%, 91%, 92%, 93%, 94%, 95%, 96%, 97%, 98% or even 99% depending on their identity to the reference sequence. Methods for determining sequence identity over such short windows are described at the NCBI web site.

Protein homologs are typically characterized by possession of at least 70%, such as at least 75%, 80%, 85%, 86%, 87%, 88%, 89%, 90%, 91%, 92%, 93%, 94%, 95%, 96%, 97%, 98% or even 99% sequence identity, counted over the full-length alignment with the amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10: 67-70). Other programs use SEG.

One of skill in the art will appreciate that these sequence identity ranges are provided for guidance only; it is possible that strongly significant homologs could be obtained that fall outside the ranges provided. Provided herein are the peptide homologs described above, as well as nucleic acid molecules that encode such homologs.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous peptides can, for example, possess at least 75%, 80%, 85%, 86%, 87%, 88%, 89%, 90%, 91%, 92%, 93%, 94%, 95%, 96%, 97%, 98% or even 99% sequence identity determined by this method. When less than the entire sequence is being compared for sequence identity, homologs can, for example, possess at least 75%, 85%, 86%, 87%, 88%, 89%, 90%, 91%, 92%, 93%, 94%, 95%, 96%, 97%, 98% or even 99% sequence identity over short windows of $10^{-20}$ amino acids. Methods for determining sequence identity over such short windows can be found at the NCBI web site. One of skill in the art will appreciate that these sequence identity ranges are provided for guidance only; it is possible that significant homologs or other variants can be obtained that fall outside the ranges provided.

Subject; Living multicellular vertebrate organisms, a category which includes both human and veterinary subjects that require an increase in the desired biological effect. Examples include, but are not limited to; humans, apes, dogs, cats, mice, rats, rabbits, horses, pigs, and cows. The term "subject" can be used interchangeably with the term "patient."

Therapeutically Effective Amount; An amount sufficient to achieve a desired biological effect, for example, an amount that is effective to decrease the size (i.e., volume), side effects and/or metastasis of prostate cancer. In one example, it is an amount sufficient to decrease the symptoms or effects of a prostate carcinoma, such as the size of the tumor. In particular examples, it is an amount effective to decrease the size of a prostate tumor and/or prostate metastasis by at least 30%, 40%, 50%, 70%, 80%, 85%, 86%, 87%, 88%, 89%, 90%, 91%, 92%, 93%, 94%, 95%, 96%, 97%, 98%, 99% or even 100% (complete elimination of the tumor).

In particular examples, it is an amount of a variant PA fusion protein effective to decrease a prostate tumor and/or an amount of prostate cancer cells lysed by a variant PA fusion protein, such as in a subject to whom it is administered, for example a subject having one or more prostate carcinomas. In other examples, it is an amount of a variant PA fusion protein and/or an amount of prostate cancer cells lysed by such a variant PA fusion protein, effective to decrease the metastasis of a prostate carcinoma.

In one embodiment, the therapeutically effective amount also includes a quantity of a variant PA fusion protein and/or an amount of prostate cancer cells lysed by a variant PA fusion protein sufficient to achieve a desired effect in a subject being treated. For instance, these can be an amount necessary to improve signs and/or symptoms a disease such as cancer, for example prostate cancer.

An effective amount of a variant PA fusion protein and/or prostate cancer cells lysed by such a variant PA fusion protein can be administered in a single dose, or in several doses, for example daily, during a course of treatment. However, the effective amount of will be dependent on the subject being treated, the severity and type of the condition being treated, and the manner of administration. For example, a therapeutically effective amount of a variant PA fusion protein can vary from about 1-10 mg per 70 kg body weight, for example about 2.8 mg, if administered iv and about $10^{-100}$ mg per 70 kg body weight, for example about 28 mg, if administered intraprostatically or intratumorally. In addition, a therapeutically effective amount of prostate cancer cells lysed by PA (variant or wild-type) can vary from about 106 to $10^8$ cells.

Therapeutically effective dose; In one example, a dose of a variant PA fusion protein sufficient to decrease tumor cell volume, such as a prostate carcinoma, in a subject to whom it is administered, resulting in a regression of a pathological condition, or which is capable of relieving signs or symptoms caused by the condition. In a particular example, it is a dose of a variant PA fusion protein sufficient to decrease metastasis of a prostate cancer.

In yet another example, it is a dose of cell lysate resulting from contact of cells with a variant PA fusion protein sufficient to decrease tumor cell volume, such as a prostate carcinoma, in a subject to whom it is administered, resulting in a regression of a pathological condition, or which is capable of relieving signs or symptoms caused by the condition. In a particular example, it is a dose of cell lysate resulting from contact of cells with a modified or wild-type PA sufficient to decrease metastasis of a prostate cancer.

Tumor; A neoplasm. Includes solid and hematological (or liquid) tumors. Examples of hematological tumors include, but are not limited to; leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (including low-, intermediate-, and high-grade), multiple myeloma, Waldenstrdm's macroglobulinemia, heavy chain disease, myelodysplastic syndrome, mantle cell lymphoma and myelodysplasia.

Examples of solid tumors, such as sarcomas and carcinomas, include, but are not limited to; fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Transformed; A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transgenic Cell; Transformed cells which contain foreign, non-native DNA.

Transgenic mammal; Transformed mammals which contain foreign, non-native DNA. In one embodiment, the non-native DNA is a modified PA which includes HSA fused to the N-terminus of PA using a prostate-specific protease cleavage site.

Variants or fragments or fusion proteins; The production of a variant PA fusion protein can be accomplished in a variety of ways (for example see Examples 12 and 16 of U.S. Pat. Nos. 7,838,266, 7,745,395, and 7,282,476, which are all incorporated herein by reference). DNA sequences which encode for a variant PA fusion protein, or a fragment or variant of a variant PA fusion protein (for example a fragment or variant having 80%, 85%, 86%, 87%, 88%, 89%, 90%, 91%, 92%, 93%, 94%, 95%, 96%, 97%, 98% or even 99% sequence identity to a variant PA fusion protein) can be engineered to allow the protein to be expressed in eukaryotic cells or organisms, bacteria, insects, and/or plants. To obtain expression, the DNA sequence can be altered and operably linked to other regulatory sequences. The final product, which contains the regulatory sequences and the therapeutic variant PA fusion protein, is referred to as a vector. This vector can be introduced into eukaryotic, bacteria, insect, and/or plant cells. Once inside the cell the vector allows the protein to be produced.

A fusion protein which includes a modified PA, (or variants, polymorphisms, mutants, or fragments thereof) linked to other amino acid sequences that do not inhibit the desired activity of the protein, for example the ability to lyse tumor cells. In one example, the other amino acid sequences are no more than 5, 6, 7, 8, 9, 10, 20, 30, or 50 amino acid residues in length. In other embodiments, a modified PA is fused to another peptide/protein that is more than 50 amino acids in length including, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600 or more.

One of ordinary skill in the art will appreciate that the DNA can be altered in numerous ways without affecting the biological activity of the encoded protein. For example, PCR can be used to produce variations in the DNA sequence which encodes a variant PA toxin. Such variants can be variants optimized for codon preference in a host cell used to express the protein, or other sequence changes that facilitate expression.

Vector; A nucleic acid molecule as introduced into a host cell, thereby producing a transformed host cell. A vector can include nucleic acid sequences that permit it to replicate in the host cell, such as an origin of replication. A vector can also include one or more selectable marker genes and other genetic elements known in the art.

II. Variant Proaerolysin Molecules

Bacterial toxins, such as aerolysin produced by *Aeromonas hydrophilia* and α-hemolysin produced by Staph *aureus*, are beta-sheet proteins that oligomerize in the plasma membrane to produce pores that lead to rapid cytolytic cell death. Pore formation physically disrupts the cell membranes, and results in death of cells in all phases of the cell cycle, including non-proliferating cells (i.e., GO arrested). However, wild-type aerolysin kills cells indiscriminately. Herein disclosed is a fusion protein comprising human serum albumin and the inactive protoxin form of aerolysin that is activated by cleavage of the activation domain with a prostate-specific protease that also cleaves the HSA bulk protein (a variant PA) that can be targeted to, and activated by, prostate cancer specific proteins. One advantage of the disclosed variant PA fusion proteins for treatment of localized and metastatic prostate cancer is that it combines a proliferation independent therapy with prostate-specific drug delivery, resulting in minimal side effects to patients. One skilled in the art will understand that other protoxins, such as *Clostridium septicum* alpha toxin, *Bacillus thuringiensis* delta-toxin, and human perforin, bouganin, *Pseudomonas* exotoxin, Bcl-2, Cholera toxin, Abrin, Ricin, Verotoxin, Diptheria toxin, Tetanus toxin, Botulinum toxin, Neural thread protein, and Ribnuclease A can be substituted for proaerolysin.

Disclosed herein are variant PA fusion proteins, including both DNA and protein sequences, which include a prostate-specific protease cleavage sequence. Such variants are also fused with albumin using at least one prostate-specific protease cleavage sequence/linker (including one, two, three, four, five or more consecutive linkers). Examples of prostate-specific protease cleavage sequences include, but are not limited to; PSA, PSMA, and HK2 cleavage sequences. The prostate-specific protease cleavage sequence functionally replaces the native furin cleavage site of wild-type PA. This replacement results in a proaerolysin variant that only becomes cytolytically active in the presence of enzymatically active proteases such as PSA, PSMA, or HK2. PSA is a serine protease with the ability to recognize and hydrolyze specific peptide sequences. It is secreted by normal and malignant prostate cells in an enzymatically active form and becomes inactivated upon entering the circulation. Since neither blood nor normal tissue other than the prostate contains enzymatically active PSA, the proteolytic activity of PSA was used to activate protoxins at sites of prostate cancer. Any PSA, PSMA, or HK2 cleavage site can be used. Examples of PSA cleavage sites include, but are not limited to, those shown in SEQ ID NOS; 5, 8, 11, and 14-21. In a particular example, the PSA cleavage site includes SEQ ID NO: 5.

In some examples, the furin cleavage site of PA (amino acids 427-432 of SEQ ID NO: 2) is deleted and a prostate-specific protease cleavage site, such as a PSA cleavage site, is inserted. In other examples, the furin cleavage site of PA is mutated and a prostate-specific protease cleavage site, such as a PSA cleavage site, inserted within, or added to the N- or C-terminus of the furin site.

Also disclosed are variant PA fusion proteins in which the PA binding domain is functionally deleted. Such variant PA fusion proteins can contain a native furin cleavage site, whereby targeting to prostate cells is achieved by functionally replacing the PA binding domain with a prostate-tissue specific binding domain. Alternatively, variant PA fusion proteins contain a prostate-specific protease cleavage site, whereby activation of the protoxin primarily occurs in cells that secrete a prostate-specific protease. The PA binding domain includes about amino acids 1-83 of SEQ ID NO: 2. The binding domain can be functionally deleted using any method known in the art, for example by deletion of all or some of the amino acids of the binding domain, such as deletion of amino acids 1-83 of SEQ ID NO: 2 or 4, or such as deletion of one or more amino acids shown as amino acids 45-66 of SEQ ID NO: 2 or 4. In other examples, the binding domain is functionally deleted by introduction of one or more site-specific mutations into the variant PA sequence, such as W45A, 147E, M57A, Y61A, and K66Q of SEQ ID NO: 2 or 4.

Variant PA fusion proteins which include a prostate-tissue specific binding domain which functionally substitutes for the native PA binding domain are disclosed. The use of one or more prostate-tissue specific binding domains can increase targeting of the disclosed variant PA fusion proteins to the prostate cells and its metastases. Several prostate-tissue specific binding domains are known. Examples include, but are not limited to a luteinizing hormone releasing hormone (LHRH) sequence, such as those shown in SEQ ID NOS; 22 and 23, and antibodies that recognize PSA and/or PSMA.

One or more prostate-tissue specific binding domains can be linked to one or more amino acids of the disclosed variant PA fusion proteins, but ideally, do not interfere significantly with the ability of the variant PA to be activated by a prostate-specific protease such as PSA, and the ability to form pores in cell membranes. For example, prostate tissue specific binding domains can be linked or inserted at an N- and/or C-terminus of a variant PA In some examples, the native binding domain of PA is deleted (i.e., amino acids 1-83 of SEQ ID NO: 2 or 4), such that attachment or linking of a prostate tissue specific binding domain to the N-terminus results in attachment to amino acid 84 of SEQ ID NO: 2 or 4. In other examples, smaller deletions or point mutations are introduced into the native binding domain of PA, such that attachment or linking of a prostate tissue specific binding domain to the N-terminus results in attachment to amino acid 1 of SEQ ID NO: 2 or 4 (or whichever amino acid is N terminal following functional deletion of the native PA binding domain). In some examples, the N-terminal amino acid of PA is changed to a Cys or other amino acid to before attaching a prostate-tissue specific binding domain, to assist in linking the prostate-tissue specific binding domain to the variant PA protein.

Alternatively or in addition, one or more prostate tissue specific binding domains can be attached or linked to other amino acids of a variant PA molecule, such as amino acid 215 or 300 of SEQ ID NO: 2 or 4. In some examples, a Cys amino acid replaces the native amino acid at that position. For example, the following changes can be made to SEQ ID NO: 2 or 4; Tyr215Cys or Ala300Cys. In one example, where the prostate tissue specific binding domain is an antibody, crosslinking can be used to attach antibodies to a variant PA, for example by reacting amino groups on the antibody with cysteine located in the PA variant (such as amino acids Cys19, Cys75, Cys159, and/or Cys164 of SEQ ID NO: 2).

Also disclosed are particular variant PA fusion proteins, such as those shown in SEQ ID NOS; 3, 4, 6, 7, 9, 10, 12, 13, 24 and 25.

In some examples the disclosed variant PA fusion proteins are linked or immobilized to a surface, such as a bead. The bead can also include a prostate-specific ligand to enhance targeting to a prostate cell, such as a localized or metastasized prostate cancer cell.

III. Human Serum Albumin

The terms, human serum albumin (HSA) and human albumin (HA) are used interchangeably herein. The terms, "albumin and "serum albumin" are broader, and encompass human serum albumin (and fragments and variants thereof) as well as albumin from other species (and fragments and variants thereof).

As used herein, "albumin" refers collectively to albumin protein or amino acid sequence, or an albumin fragment or variant, having one or more functional activities (e.g., biological activities) of albumin. In particular, "albumin" refers to human albumin or fragments thereof (see EP 201 239, EP 322 094 WO 97/24445, WO95/23857) or albumin from other vertebrates or fragments thereof, or analogs or variants of these molecules or fragments thereof.

As used herein, the albumin portion of the fusion protein may comprise the full length of the sequence as shown in SEQ ID NO: 27, or may include one or more fragments thereof that are capable preventing, substantially reducing or reducing binding of the recombinant PRX302 pro-drug protein to GPI-anchored proteins on normal cells in the blood or host tissues. In one embodiment, the HA protein fragment comprises the N-terminal end of HA. In another embodiment, the HA protein fragment comprises the C-terminal end of HA. In particular embodiments, HA fragments may comprise 10 or more amino acids in length or may comprise about 15, 20,25, 30, 50, or more contiguous amino acids from the HA sequence or may include part or all of specific domains of HA. For instance, one or more fragments of HA spanning the first two immunoglobulin-like domains may be used.

The albumin portion of the albumin fusion proteins of the invention may be a variant of normal HA. The term "variants" includes insertions, deletions and substitutions, either conservative or non-conservative, where such changes do not substantially alter one or more of the oncotic, useful ligand-binding and non-immunogenic properties of albumin.

In particular, the albumin fusion proteins of the invention may include naturally occurring polymorphic variants of human albumin and fragments of human albumin, for example those fragments disclosed in EP 322 094 (namely HA (Pn), where n is 369 to 419). The albumin may be derived from any vertebrate, especially any mammal, for example human, cow, sheep, or pig. Non-mammalian albumins include, but are not limited to, hen and salmon. The albumin portion of the fusion protein may be from a different animal than the PRC302 portion.

Generally speaking, an HA fragment or variant will be at least 100 amino acids long, preferably at least 150 amino acids long. The HA variant may consist of or alternatively comprise at least one whole domain of HA, for example domains 1 (amino acids 1-194 of SEQ ID NO: 27), 2 (amino acids 195-387 of SEQ ID NO: 27), 3 (amino acids 388-585 of SEQ ID NO: 27), 1+2 (1-387 of SEQ ID NO: 27), 2+3 (195-585 of SEQ ID NO: 27 (amino acids 1-194 of SEQ ID NO:27+amino acids 388-585 of SEQ ID NO: 27). Each domain is itself made up of two homologous subdomains namely 1-105, 120-194, 195-291, 316-387, 388-491 and 512-585, with flexible inter-subdomain linker regions comprising residues Lys106 to Glu119, Glu292 to Val315 and Glu492 to Ala511.

In certain embodiments, the albumin portion of an albumin fusion protein of the invention comprises at least one subdomain or domain of HA or conservative modifications thereof.

The present invention relates generally to fusion proteins comprising albumin and methods of treating, preventing, or ameliorating diseases or disorders. A fusion protein comprising albumin refers to a protein formed by the fusion of at least one molecule of albumin (or a fragment or variant thereof) to at least one molecule of a PRX302 protein (or fragment or variant thereof). An albumin-PA or albumin-PRX302 fusion protein comprises at least a fragment or variant of a PA protein and at least a fragment or variant of human serum albumin, which are associated with one another, preferably by genetic fusion (i.e., the albumin fusion protein is generated by translation of a nucleic acid in which a polynucleotide encoding all or a portion of a PA/PRX302 protein is joined in-frame with a polynucleotide encoding all or a portion of albumin) or chemical conjugation to one another. The PA/PRX302 protein and albumin protein, once part of the fusion protein, may be referred to as a "portion", "region" or "moiety" of the fusion protein.

In one embodiment, the invention provides a fusion protein comprising, or alternatively consisting of, a PA/PRX302 protein and a serum albumin protein. In other embodiments, the invention provides a fusion protein comprising, or alternatively consisting of, a biologically active and/or therapeutically active fragment of a PA/PRX302 protein and a serum albumin protein. In other embodiments, the invention provides a fusion protein comprising, or alternatively consisting of, a biologically active and/or therapeutically active variant of a PA/PRX302 protein and a serum albumin protein. In particular embodiments, the serum albumin protein component of the fusion protein is the mature portion of serum albumin.

In further embodiments, the invention provides a fusion protein comprising, or alternatively consisting of, a PA/PRX302 protein, and a biologically active and/or therapeutically active fragment of serum albumin. In further embodiments, the invention provides a fusion protein comprising, or alternatively consisting of, a PA/PRX302 protein and a biologically active and/or therapeutically active variant of serum albumin. In certain embodiments, the PA/PRX302 protein portion of the fusion protein is the full length of the PA/PRX302 protein.

In further embodiments, the invention provides a fusion protein comprising or alternatively consisting of, a biologically active and/or therapeutically active fragment or variant of a PA/PRX302 protein and a biologically active and/or therapeutically active fragment or variant of serum albumin. In some embodiments, the invention provides a fusion protein comprising, or alternatively consisting of, the mature portion of a PA/PRX302 protein and the mature portion of serum albumin.

In specific embodiments, the fusion protein comprises HA as the N-terminal portion, and a PA/PRX302 protein as the C-terminal portion. Alternatively, a fusion protein comprising HA as the C-terminal portion, and a PA/PRX302 protein as the N-terminal portion may also be used.

In other embodiments, the fusion protein has a PA/PRX302 protein fused to both the N-terminus and the C-terminus of albumin. In one embodiment, the PA/PRX302 proteins fused at the N- and C-termini are the same PA/PRX302 proteins. In other embodiments, the PA/PRX302 proteins fused at the N- and C-termini are different PA/PRX302 proteins or just different proteins. In another embodiment, the PA/PRX302 proteins fused at the N- and C-termini are different therapeutic proteins which may be used to treat or prevent the same disease, disorder, or condition.

In addition to the fusion protein in which the albumin portion is fused N-terminal and/or C-terminal of the PA/PRX302 protein portion, fusion proteins of the invention may also be produced by inserting the PA/PRX302 protein or peptide of interest into an internal region of HA. For instance, within the protein sequence of the HA molecule a number of loops or turns exist between the end and beginning of α-helices, which are stabilized by disulphide bonds. The loops, as determined from the crystal structure of HA (PDB identifiers 1AO6, 1BJ5, 1BKE, IBM0, 1E7E to 1E71 and 1UOR) for the most part extend away from the body of the molecule. These loops are useful for the insertion, or internal fusion, of therapeutically active peptides, particularly those requiring a secondary structure to be functional, or PA/PRX302 proteins, to essentially generate an albumin molecule with specific biological activity.

Loops in human albumin structure into which peptides or polypeptides may be inserted to generate albumin fusion proteins of the invention include; Val54-Asn61, Thr76-

Asp89, Ala92-Glu100, Gln170-Alal76, His247-Glu252, Glu266-Glu277, Glu280-His288, Ala362-Glu368, Lys439-Pro447, Val462-Lys475, Thr478-Pro486, and Lys50G-Thr566. In specific embodiments, peptides or polypeptides are inserted into the Val54-Asn61, Gin170-Ala176, and/or Lys560-Thr566 loops of mature human albumin (SEQ ID NO: 27).

IV. Treatment of Prostate Cancer Using Modified Proaerolysin Fusion Proteins

The variant PA fusion proteins comprising variant PA and albumin disclosed and discussed above are specifically activated to potent cytotoxins within prostate cancer sites via the proteolytic activity of prostate-specific proteases such as PSA, PSMA, and HK2. Targeting in some examples is achieved by including one or more prostate-tissue specific binding domains, such as LHRH peptide which can bind to its cognate LHRH receptor expressed by prostate cancer cells, or PSMA or LHRH antibodies, which can bind to PSMA or LHRH expressed on the surface of prostate cancer cells. One skilled in the art will recognize that the use of an albumin-variant PA fusion protein which includes a furin cleavage site and an LHRH peptide or antibody, can be used to treat other cancers which express LHRH receptors, such as melanoma and cancers of the breast, ovary and lung, using the albumin-variant PA fusion proteins and methods disclosed herein. Furthermore, one skilled in the art will recognize that the use of an albumin-variant PA fusion protein which includes a furin or PSMA cleavage site, and/or a PSMA antibody, can be used to treat other cancers in which PSMA is expressed (e.g. in the vasculature of the tumor), such as cancers of the breast, colon, kidney, bladder and brain, using the variant albumin-variant PA fusion proteins and methods disclosed herein.

The disclosed albumin-variant PA fusion proteins, such as nucleic acids and/or proteins, can be administered systemically or locally using any method known in the art, to subjects having localized or metastatic prostate cancer. In addition, the disclosed albumin-variant PA fusion proteins can be administered to a subject for immunostimulatory therapy. Due to the specificity of binding and activation of the disclosed albumin-variant PA fusion proteins, local and systemic administration should have minimal effect on a patient's normal tissues and ideally produce little to no side effects.

In one example, the disclosed albumin-variant PA fusion proteins are injected into the prostate gland (intraprostatically) and/or into the prostate tumor (intratumorally) in a subject having prostate cancer, such as a localized tumor. Such localized injection and subsequent lysis of prostate cancer cells within the prostate gland can produce an immunostimulatory effect leading to a decrease or elimination of micrometastatic disease in treated subjects. In this way, systemic disease is treated or reduced through a minimally toxic, locally applied therapy.

In addition, or alternatively, the disclosed albumin-variant PA fusion proteins can be administered systemically, for example intravenously, intramuscularly, subcutaneously, or orally, to a subject having prostate cancer, such as a metastatic prostate tumor. Systemic therapy can also have an immunostimulatory anti-tumor effect. The disclosed albumin-variant PA fusion proteins which include a PSA-cleavage site are not hydrolyzed by serum proteases or enzymatically inactive PSA within the blood. Instead, the unhydrolyzed disclosed variant PA fusion proteins are delivered via the blood to the extracellular fluid within metastatic cancer deposits where they can be hydrolyzed to the active therapeutic toxin by the enzymatically active PSA secreted by these prostate cancer cells. Once hydrolyzed, the liberated toxin enters PSA-producing and non-producing bystander cells in the immediate vicinity due to its high membrane penetrating ability and induces the cytolytic death of these cells.

An additional method for systemically treating prostate cancer in a subject is also disclosed. In this method, prostate cancer cells are removed from the subject having prostate cancer, such as a metastatic prostate tumor. Alternatively or in addition, established prostate cancer cell lines can be used. Examples of prostate cancer cell lines that can be used include, but are not limited to; PSA-producing cells such as LNCaP (such as ATTC Nos. CRL-1740) and CRL-10995) and CWR22R (ATCC CRL-2505 and Nagabhushan et al., Cancer Res. 56 (13); 3042-6, 1996), or PSA non-producing cells such as PC-3 (ATCC CRL-1435) and DU 145 (ATCC HTB-81). The removed cells or cell lines are incubated or contacted with the disclosed albumin-variant PA fusion proteins. This incubation results in lysis of the cells by the albumin-variant PA fusion proteins, and production of a cell lysate which is administered to the subject. In one example, the method further includes administration of immunostimulatory factors, lysates from prostate cancer cells engineered to produce immunostimulatory factors, and/or irradiated prostate cancer cells (including prostate cancer cells engineered to produce immunostimulatory factors). Examples of immunostimulatory factors include, but are not limited to; granulocyte macrophage colony stimulatory factor (GM-CSF); members of the interleukin family of proteins such as but not limited to interleukin-2 and interleukin-6, granulocyte colony stimulatory factor (G-CSF); and members of interferon family such as interferon alpha, beta or gamma. Administration of such materials to a subject can be simultaneous with the cell lysate (co-administration), before administration of the cell lysate, and/or subsequent to administration of the cell lysate.

In one example, such administration enhances the ability of a subject to decrease the volume of a prostate tumor and/or a metastatic tumor. For example, the disclosed methods can reduce prostate tumor cell volume and/or a metastatic tumor cell volume, such as by at least 10%, at least 20%, at least 30%, at least 40%, at least 50%, at least 60%, at least 70%, at least 80%, at least 85%, at least 90%, at least 95% or more. In addition, the disclosed methods can result in a decrease in the symptoms associated with a prostate tumor and/or a metastatic prostate tumor.

The disclosed albumin-variant PA fusion proteins can be administered as a single modality therapy or used in combination with other therapies, such as radiation therapy and/or androgen ablative therapies (such as LHRH receptor agonists/antagonists, antiandrogens, estrogens, adrenal steroid synthesis inhibitors ketoconazole and aminoglutethimide). In addition, administration of the disclosed albumin-variant PA fusion proteins can be alone, or in combination with a pharmaceutically acceptable carrier, and/or in combination with other therapeutic compounds, such as those that reduce the production of antibodies to the administered variant PA proteins (for example Rituximab and steroids) and other anti-tumor agents.

Without further elaboration, it is believed that one skilled in the art, using the preceding description, can utilize the present invention to the fullest extent. The following examples are illustrative only, and not limiting of the remainder of the disclosure in any way whatsoever.

V. Other Proteases and Macromolecules

The present invention also provides proaerolysin fusion proteins that are activated by proteases other than PSA and/or conjugated to macromolecules other than HSA. Examples of proteases that can be used in a fusion protein include, but are not limited to, caspase 3, cathepsin B, carboxypeptidase, fibroblast activation protein, MMP-2/-9/-14, MMP7, plasmin, thimet oligopeptiase, uPA, cathepsin K, thrombin, and trypsin. The cleavage site sequences of such proteases are known in the art. Other macromolecules that can be used in place of HSA include, but are not limited to, polyethylene glycol (PEG), N-(2-hydroxypropyl) methacrylamide copolymer (HPMAcp), and dextran.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

BACKGROUND

To overcome tumor cell heterogeneity based therapeutic resistance of prostate cancer, a strategy was developed by the Denmeade/Isaacs labs to synthesize "molecular grenades" that are designed to efficiently "detonate" (i.e., release a highly potent killing entity) within the extracellular fluid only at sites of prostate cancer (1). The chemical engineering requirements for this strategy are that; 1) the killing entity be a highly potent inhibitor of such an essential intracellular process that this inhibition kills all cell types without the development of resistance, 2) this killing entity be capable of coupling via a peptide bond to a specifically engineered linker peptide producing an initially inactive "molecular grenade", and 3) the sequence of this linker peptide is designed so that its efficient hydrolysis and thus liberation of the killing entity is restricted to active enzymes present only in the extracellular fluid at sites of metastatic prostate cancer. Thus, when such a chemically engineered "molecular grenade" is infused, it distributes systemically throughout the body but can only be activated (i.e., detonated) by a protease expressed within the extracellular fluid (ECF) within metastatic sites of prostate cancer, but not within sites of non-prostate normal tissue. Within tumor sites, the protease "pulls the pin" on the grenade by proteolytically releasing the highly potent killing entity.

The advantage of such selective extracellular hydrolysis is that only a fraction of the cancer cells need to express the enzyme since its continuous activity amplifies the level of the killing toxin liberated within the ECF shared by all cells within the metastatic site. This amplification minimizes the problem of tumor cell heterogeneity by inducing a substantial "bystander effect" in which, like a detonated grenade, all cells within the tumor site including both malignant and infiltrating host supportive cells are killed, even those that do not express the activating enzyme. Thus, development of resistance is retarded without simultaneously producing non-selective host toxicity.

For this application, we are focused upon using as the killing entity the bacterial toxin proaerolysin (PA). PA is produced and secreted by the aquatic Gram-negative bacteria Aeromonas hydrophilia and is ideally suited for such recombinant modification. These bacteria synthesize the 53-kDa PA protein and secrete it as a water soluble dimer. PA contains a number of separate domains that include an N-terminal GPI-anchored protein binding domain, a "toxin" domain responsible for pore formation, a protease activation domain and a C-terminal inhibitory peptide that renders the toxin inactive until it is proteolytically released (2).

The natural protease activation domain is a six amino acid sequence that is a proteolytic substrate for ubiquitous furin-like proteases produced by many cell types. Hydrolysis of the activation domain by furin liberates the C-terminal inhibitory peptide converting inactive PA into cytotoxic aerolysin. Activated aerolysin binds to GPI-anchored proteins in the cell membrane and inserts into the membrane forming a highly stable ~17 Å heptamer channel, which leads to rapid cell swelling and resultant osmotic cell death which is proliferation independent and without a mechanism for the development of resistance (2).

Most mammalian cells, with the exception of erythrocytes, produce the necessary furin protease required to activate proaerolysin (2). Once activated, wild-type aerolysin is toxic to mammalian cells, including erythrocytes, at picomolar concentrations. In our laboratory, wild-type PA is toxic to all human prostate cancer cell lines (i.e., PC-3, DU145, LNCaP, LAPC-4, CWR22Rv1) and human non-prostate cancer cell lines [i.e., TSU (bladder origin) SN12C (renal cell), TT (medullary thyroid) ] with LD50 values of 50 picomolar or less (2).

As expected from its mechanism of cytotoxicity, PA is very toxic in vivo. Following a single intravenous dose, the LD100 (i.e., the dose that kills 100% of animals within 24 hrs) in mice, is 0.1 μg (2). Thus, PA must be modified to target its killing ability to sites of prostate cancer without producing unacceptable host toxicity. An enabling principle for such a "molecular grenade" approach is that only normal and malignant prostate epithelial cells synthesize and secrete high amounts of enzymatically active Prostate Specific Antigen (PSA) into their ECF (3). Once in the ECF, enzymatically active PSA eventually enters the blood where it is inactivated by binding to major serum protease inhibitors [i.e., al-antichymotrypsin and a2-macroglobulin] for PSA (3). Therefore, the only location in the body besides the prostate in which PSA is enzymatically active is in the ECF within sites of prostate cancers (3).

Previously, we identified a specific 7 amino-acid peptide sequence (i.e., HSSKLQ, SEQ ID NO: 2) that is efficiently and selectively cleaved after Q by PSA (3). To allow selective PSA proteolysis and thus activation, the present inventors genetically engineered a bacterially produced recombinant PA in which the furin cleavage sequence was subjected to site-directed mutagenesis using polymerase chain reaction to convert it to a PSA-cleavable sequence [HSSKLQ] (2). The mutated gene was then subcloned into the pMMB66HE vector for amplification in Escherichia coli. This construct was then transferred to a protease-deficient strain of A. salmonicida that facilitates the production of large amounts of uncontaminated PRX302. This modified toxin, termed PRX-302 is activated in culture by PSA producing prostate cancer cells resulting in potent cell killing (i.e., LD50 values of less than 200 picoMolar, but only against PSA producing cancer lines) (2). When as little as 100 picomoles of PXR302 is injected directly into PSA expressing human prostate cancer xenografts in nude mice, sufficient hydrolysis of the protoxin occurs in the extracellular fluid via enzymatically active PSA to produce more than a 50% regression of the cancer in all animals by 2 weeks post injection with 25% of the injected animal having a complete regression by a month post treatment (2). In contrast, no tumor regression is produced if PRX302 is injected intra-tumorally into non-PSA producing non-prostate cancers (2).

While PRX302 is highly water-soluble, PSA-activation releases the C-terminal inhibitory peptide causing a conformational change in the protein that exposes hydrophobic domains that result in rapid membrane insertion. Therefore, once activated in the extracellular fluid at sites of prostate cancer, very little of the aerolysin toxin leaks back into the systemic circulation limiting the non-specific toxicity to host tissue. This was documented by preclinical studies demonstrating that intraprostatic injection into the PSA-producing monkey prostate produced no toxicity in periprostatic tissues, including the lateral pelvic fascia, anal sphincter, urethra, urinary bladder, or rectum or other distant organs (2).

Based on efficacy and safety in these preclinical studies, PRX302 has undergone an open-label phase 1 dose-escalation trial to assess the safety of transperineal injection of PRX302 as therapy for local radiation-recurrent prostate cancer or BPH (4). Subsequently, a phase 2 volume-escalation study was performed to evaluate the effect of PRX302 on alleviating lower urinary tract systems in men with moderate to severe BPH. The results of these phase II trial have been reported recently and document the safety and therapeutic activity of a single transperineal, intraprostatic treatment of PRX302 over a follow-up period of a year (4).

Presently, more than 120 patients have received PRX302 which is entering phase III registration trials as local therapy for symptomatic BPH. Based upon these encouraging clinical results for local delivery of PRX302, the possibility that a therapeutic effect is produced when the PRX302 is administered systemically was tested. Because the modified toxin is injected intravenously when administered for systemic treatment of metastatic prostate cancer, we determined whether PRX302 is stable to non-specific activation in normal and PSA-containing human plasma utilizing a sensitive hemolysis assay. These studies documented that pre-incubation of the PRX302 with enzymatically active PSA in aqueous buffer alone prior to adding RBC's results in ~45% hemolysis. To assess whether PRX302 becomes activated in either normal human plasma or plasma from prostate cancer patients with elevated PSA, PRX302 (50 ng/ml) was added to both 50% unmodified human plasma and 50% plasma pre-incubated with 10,000 ng/ml of enzymatically active PSA in order for the PSA to form enzymatically inactive complexes with serum protease inhibitors, and then the plasma was incubated with human red blood cells (2% v/v). The addition of PRX302 to human plasma or human plasma spiked with high concentration of PSA results in no appreciable hemolysis (i.e., <1% of Triton control). These results demonstrate that the PRX302 can be administered systemically without any significant activation in the blood even when it contains an extremely high level (i.e., 10,000 ng/ml) of measureable but inactivated PSA.

Next, we determined the maximally tolerated systemic dose of wild type PA vs. PRX302 when given IV to nude mice. The wild type PA is highly toxic to mice. An intravenous dose of 1 μg causes death within one hour and the LD100 at 24 hrs following a single IV injection is 0.1 μg. In contrast, the LD100 of a single IV injection of the PRX302 at 24 hrs post injection was found to be 25-fold higher (i.e., 2.5 μg total dose). Additional experiments, however, demonstrated that mice could only be safely injected with 1 μg daily of PRX302 for 5 consecutive days without significant toxicity. Higher doses resulted in animal deaths ~1 week after multiplied daily doses >1 μg. Preliminary studies are consistent with the dose limiting in vivo toxicity of the wild type and modified PRX302 being due to its binding to GPI-anchor proteins expressed by most mammalian cell types. Nude mice bearing the LNCaP human prostate cancer were given the maximally tolerated dose regimen of 1 μg/day of PRX302 given IV for 5 days. In this experiment there was no significant difference in LNCaP tumor size out to 20 days post-therapy in the PRX302 treated group vs. controls.

While PRX302 is effective as local therapy for prostate cancer, these latter results illustrate that it is not possible to give sufficient PRX302 systemically to achieve an effective level within sites of prostate cancer without producing unacceptable host toxicity due to its binding to GPI-anchor proteins ubiquitously expressed on cells in the host normal tissue.

Experimental Design

Previous studies document that the binding to the GPI-anchor protein involves a surface composed of regions of domain 1 (i.e., which includes the N-terminus) and domain 2 of PA and that when a bulky protein is fused to the N-terminal, such binding is prevented (5). These results raise the possibility that by fusing a bulky protein to the N-terminus of PRX302, binding to the GPI-anchor can be prevented thus allowing the variant PRX302 protein to be delivered systemically without non-specific GPI-dependent uptake by normal tissues. This raises the questions of both what "bulky protein" and how should it be coupled in such a recombinant variant protein so that the "bulky protein" can be hydrolyzed off to selectively liberate PRX302 with its GPI-anchor binding surface free to bind to GPI-anchors only on cells in sites of metastatic prostate cancer.

Along these lines, human serum albumin (HSA) is an ideal candidate. HSA is the most abundant plasma protein (35-50 g/L serum protein) and has a molecular weight of 67 kDa and serum half-life of 20 days. Tumors trap plasma proteins and utilize their degradation products for proliferation (6). Pharmacokinetic profiling documented that such tumor uptake is correlated with both serum half-life and protein weight. Such tumor uptake, tumor blood flow and the transport of molecules in the interstitium led Maeda and Matsumura to coin the expression "EPR" (i.e., enhanced permeability and retention of macromolecules) in relation to passive tumor targeting of serum proteins. The leaky defective blood vessels of tumor tissue make its vasculature permeable for macromolecules whereas in blood vessels of healthy tissue only small molecules can pass the endothelial barrier. The pore size of tumor microvessels varies from 100 to 1200 nm in diameter and serum albumin has an effective diameter of 7.2 nm allowing extravasation into tumor tissue but not into normal tissue (6).

Thus, the hypothesis for this application is that the C-terminus of HSA can be fused via a PSA cleavable peptide linker (i.e., HSSKLQ, SEQ ID NO: 2) to the N-terminus of PRX302 to generate a novel recombinant PRX302 protein which will not bind to GPI-anchored proteins on normal cells in the blood or host tissues. Instead, it will accumulate via an EPR effect within sites of metastatic prostate cancer where enzymatically active PSA in the extracellular fluid will hydrolyze the HSA linker liberating PRX302. Additionally, PSA will also remove the C-terminal inhibitory peptide from PRX302 to generate aerolysin monomers which can oligomerize to form the heptameric pores that will result in selective killing of cells only in the site of metastatic prostate cancer.

REFERENCES

1. Denmeade S R, Isaacs J T. Engineering enzymatically activated "molecular grenades" for cancer. Oncotarget 2012; 3: 666-7.
2. Williams S A, Merchant R F, Garrett-Mayer E, Isaacs J T, Buckley J T, Denmeade S R. A prostate-specific antigen-activated channel-forming toxin as therapy for prostatic disease. J Natl Cancer Inst. 2007; 99: 376-85.
3. Denmeade S R, Sokoll L J, Chan D W, Khan S R, Isaacs J T. Concentration of enzymatically active prostate-specific antigen (PSA) in the extracellular fluid of primary human prostate cancers and human prostatic cancer xenograft models. Prostate 2001; 48:1-6.
4. Denmeade S R, Egerdie B, Steinhoff, et al. Phase land 2 studies demonstrate the safety of intraprostatic injection of PXR302 for the targeted treatment of lower urinary tract symptoms secondary to benign prostatic hyperplasia. Eur Urol 2011; 59:747-54.
5. Osusky M, Teschke L, Wang X et al. A chimera of interleukin 2 binding variant of aerolysin is selectively toxic to cells displaying the interleukin 2 receptor. J Biol Chem 2008; 283: 1572-1579.
6. Kratz F. Albumin as a drug carrier; design of prodrugs, drug conjugates, and nanoparticles. J Controlled Release 2008; 132: 171-183.
7. Denmeade S R. Mhaka A M. Rosen D M. Brennen W N. Dalrymple S P. Dach I. Olesen Claus. Gurel B. DeMarzo A M. Wilding G. Carducci M A. Dionne C A. Møller J V. Nissen P. Christensen S B. Isaacs J T. Engineering a Prostate-specific Membrane Antigen-Activated Tumor Endothelial Cell Prodrug for Cancer Therapy. Sci Trans Med 2012; 4; 140ra86.

We claim:

1. A method of treating prostate cancer or benign prostatic hyperplasia (BPH) in a subject, comprising administering to the subject an effective amount of a prodrug composition comprising;
   a. a prostate-specific antigen (PSA)-activated pro-aerolysin (PA), wherein a PSA cleavable linker replaces the native furin cleavage site within PA comprising SEQ ID NO: 2; and
   b. human serum albumin (HSA), or a fragment thereof, fused to the N-terminus of the PSA-activated PA with a linker sequence comprising at least one PSA cleavable site,
   wherein the prodrug composition is administered systemically, and
   wherein the prodrug does not bind to GPI-anchored proteins on normal cells thereby lowering non-specific toxicity in subject tissues as compared to administration of the PSA-activated PA alone.

2. The method of claim 1, wherein the PSA cleavable linker comprises SEQ ID NO: 5.

3. The method of claim 1, wherein the PSA cleavable linker replaces the amino acids at position 427-432 of SEQ ID NO: 2.

4. The method of claim 1, wherein the at least one PSA-cleavable site comprises SEQ ID NO: 5.

5. The method of claim 1, wherein the HSA or fragment thereof is fused to the N-terminus of the PSA-activated PA with a linker sequence comprising four PSA cleavable sites having SEQ ID NO: 5.

6. The method of claim 1, wherein the human serum albumin (HSA), or a fragment thereof, comprises SEQ ID NO: 27, or a fragment of at least 100 amino acids.

7. The method of claim 6, wherein the prostate-specific antigen (PSA)-activated pro-aerolysin (PA) comprises SEQ ID NO: 4.

8. The method of claim 1, wherein the human serum albumin (HSA), or a fragment thereof, comprises SEQ ID NO: 27, or at least one whole domain thereof.

9. The method of claim 8, wherein the prostate-specific antigen (PSA)-activated pro-aerolysin (PA) comprises SEQ ID NO: 4.

10. The method of claim 1, wherein the prostate-specific antigen (PSA)-activated pro-aerolysin (PA) comprises SEQ ID NO: 4.

* * * * *

SEQUENCE LISTING

```
<160> NUMBER OF SEQ ID NOS: 48

<210> SEQ ID NO 1
<211> LENGTH: 1410
<212> TYPE: DNA
<213> ORGANISM: Aeromonas hydrophila

<400> SEQUENCE: 1
gcagagcccg tctatccaga ccagcttcgc ttgttttcat tgggccaagg ggtctgtggc      60
gacaagtatc gccccgtcaa tcgagaagaa gcccaaagcg ttaaaagcaa tattgtcggc     120
atgatggggc aatggcaaat aagcgggctg gccaacggct gggtcattat ggggccgggt     180
tataacggtg aaataaaacc agggacagcg tccaatacct ggtgttatcc gaccaatcct     240
gttaccggtg aaataccgac actgtctgcc ctggatattc cagatggtga cgaagtcgat     300
gtgcagtggc gactggtaca tgacagtgcg aatttcatca aaccaaccag ctatctggcc     360
cattacctcg gttatgcctg ggtgggcggc aatcacagcc aatatgtcgg cgaagacatg     420
gatgtgaccc gtgatggcga cggctgggtg atccgtggca acaatgacgg cggctgtgac     480
ggctatcgct gtggtgacaa gacggccatc aaggtcagca acttcgccta taacctggat     540
cccgacagct tcaagcatgg cgatgtcacc cagtccgacc gccagctggt caagactgtg     600
gtgggctggg cggtcaacga cagcgacacc ccccaatccg gctatgacgt caccctgcgc     660
tacgacacag ccaccaactg gtccaagacc aacacctatg gcctgagcga gaaggtgacc     720
accaagaaca agttcaagtg gccactggtg ggggaaaccc aactctccat cgagattgct     780
gccaatcagt cctgggcgtc ccagaacggg ggctcgacca ccacctccct gtctcagtcc     840
gtgcgaccga ctgtgccggc ccgctccaag atcccggtga agatagagct ctacaaggcc     900
gacatctcct atccctatga gttcaaggcc gatgtcagct atgacctgac cctgagcggc     960
ttcctgcgct ggggcggcaa cgcctggtat acccacccgg acaaccgtcc gaactggaac    1020
cacaccttcg tcataggtcc gtacaaggac aaggcgagca gcattcggta ccagtgggac    1080
aagcgttaca tcccgggtga agtgaagtgg tgggactgga actggaccat acagcagaac    1140
ggtctgtcta ccatgcagaa caacctggcc agagtgctgc gcccggtgcg ggcggggatc    1200
accggtgatt tcagtgccga gagccagttt gccggcaaca tagagatcgg tgctcccgtg    1260
```

-continued

```
ccgctcgcgg ctgacagcaa ggtgcgtcgt gctcgcagtg tggacggcgc tggtcaaggc      1320
ctgaggctgg agatcccgct cgatgcgcaa gagctctccg ggcttggctt caacaacgtc      1380
agcctcagcg tgacccctgc tgccaatcaa                                        1410
```

<210> SEQ ID NO 2
<211> LENGTH: 470
<212> TYPE: PRT
<213> ORGANISM: Aeromonas hydrophila

<400> SEQUENCE: 2

```
Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
            115                 120                 125

Gly Gly Asn His Ser Gln Tyr Val Gly Glu Asp Met Asp Val Thr Arg
        130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
```

```
                340              345               350
Ser Ser Ile Arg Tyr Gln Trp Asp Lys Arg Tyr Ile Pro Gly Glu Val
        355                 360               365

Lys Trp Trp Asp Trp Asn Trp Thr Ile Gln Gln Asn Gly Leu Ser Thr
    370             375              380

Met Gln Asn Asn Leu Ala Arg Val Leu Arg Pro Val Arg Ala Gly Ile
385             390             395               400

Thr Gly Asp Phe Ser Ala Glu Ser Gln Phe Ala Gly Asn Ile Glu Ile
            405             410               415

Gly Ala Pro Val Pro Leu Ala Ala Asp Ser Lys Val Arg Arg Ala Arg
            420             425             430

Ser Val Asp Gly Ala Gly Gln Gly Leu Arg Leu Glu Ile Pro Leu Asp
        435             440             445

Ala Gln Glu Leu Ser Gly Leu Gly Phe Asn Asn Val Ser Leu Ser Val
    450             455             460

Thr Pro Ala Ala Asn Gln
465             470

<210> SEQ ID NO 3
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.

<400> SEQUENCE: 3
gcagagcccg tctatccaga ccagcttcgc ttgtttttcat tgggccaagg ggtctgtggc      60
gacaagtatc gccccgtcaa tcgagaagaa gcccaaagcg ttaaaagcaa tattgtcggc     120
atgatggggc aatggcaaat aagcgggctg gccaacggct gggtcattat ggggccgggt     180
tataacggtg aaataaaacc agggacagcg tccaatacct ggtgttatcc gaccaatcct     240
gttaccggtg aaataccgac actgtctgcc ctggatattc cagatggtga cgaagtcgat     300
gtgcagtggc gactggtaca tgacagtgcg aatttcatca aaccaaccag ctatctggcc     360
cattacctcg gttatgcctg ggtgggcggc aatcacagcc aatatgtcgg cgaagacatg     420
gatgtgaccc gtgatggcga cggctgggtg atccgtggca caatgacggc ggctgtgac     480 ggctatcgct gtggtgacaa gacggccatc aaggtcagca acttcgccta taacctggat     540
cccgacagct tcaagcatgg cgatgtcacc agtccgacc gccagctggt caagactgtg     600
gtgggctggg cggtcaacga cagcgacacc ccccaatccg gctatgacgt caccctgcgc     660
tacgacacag ccaccaactg gtccaagacc aacacctatg cctgagcga gaaggtgacc     720 accaagaaca gttcaagtg ccactggtg ggggaaaccc aactctccat cgagattgct     780
gccaatcagt cctgggcgtc ccagaacggg ggctcgacca ccacctcccct gtctcagtcc     840 gtgcgaccga ctgtgccggc ccgctccaag atcccggtga agatagagct ctacaaggcc     900
gacatctcct atccctatga gttcaaggcc gatgtcagct atgacctgac cctgagcggc     960
ttcctgcgct ggggcggcaa cgcctggtat acccacccgg acaaccgtcc gaactggaac    1020
cacaccttcg tcataggtcc gtacaaggac aaggcgagca gcattcggta ccagtgggac    1080
aagcgttaca tcccgggtga agtgaagtgg tgggactgga actggaccat acagcagaac    1140
ggtctgtcta ccatgcagaa caacctggcc agagtgctgc gccggtgcg ggcggggatc    1200 accggtgatt tcagtgccga gagccagttt gccggcaaca tagagatcgg tgctcccgtg    1260
```

-continued

```
ccgctcgcgg ctgacagcca ttcctccaag ctgcagagtg tggacggcgc tggtcaaggc     1320
ctgaggctgg agatcccgct cgatgcgcaa gagctctccg ggcttggctt caacaacgtc     1380
agcctcagcg tgacccctgc tgccaatcaa                                       1410

<210> SEQ ID NO 4
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 4

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
    210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
        275                 280                 285

Ser Lys Ile Pro Val Lys Ile Glu Leu Tyr Lys Ala Asp Ile Ser Tyr
    290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335
```

-continued

```
Pro Asn Trp Asn His Thr Phe Val Ile Gly Pro Tyr Lys Asp Lys Ala
        340                 345                 350

Ser Ser Ile Arg Tyr Gln Trp Asp Lys Arg Tyr Ile Pro Gly Glu Val
        355                 360                 365

Lys Trp Trp Asp Trp Asn Trp Thr Ile Gln Gln Asn Gly Leu Ser Thr
        370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Ser His Ser Ser Lys Leu Gln
                420                 425                 430

Ser Val Asp Gly Ala Gly Gln Gly Leu Arg Leu Glu Ile Pro Leu Asp
        435                 440                 445

Ala Gln Glu Leu Ser Gly Leu Gly Phe Asn Asn Val Ser Leu Ser Val
        450                 455                 460

Thr Pro Ala Ala Asn Gln
465                 470
```

```
<210> SEQ ID NO 5
<211> LENGTH: 6
<212> TYPE: PRT
<213> ORGANISM: Homo sapiens

<400> SEQUENCE: 5

His Ser Ser Lys Leu Gln
1               5

<210> SEQ ID NO 6
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.

<400> SEQUENCE: 6
gcagagcccg tctatccaga ccagcttcgc ttgtttttcat tgggccaagg ggtctgtggc      60
gacaagtatc gccccgtcaa tcgagaagaa gcccaaagcg ttaaaagcaa tattgtcggc     120
atgatggggc aatggcaaat aagcgggctg gccaacggct gggtcattat ggggccgggt     180
tataacggtg aaataaaacc agggacagcg tccaatacct ggtgttatcc gaccaatcct     240
gttaccggtg aaataccgac actgtctgcc ctggatattc cagatggtga cgaagtcgat     300
gtgcagtggc gactggtaca tgacagtgcg aatttcatca aaccaaccag ctatctggcc     360
cattacctcg gttatgcctg ggtgggcggc aatcacagcc aatatgtcgg cgaagacatg     420
gatgtgaccc gtgatggcga cggctgggtg atccgtggca acaatgacgg cggctgtgac     480
ggctatcgct gtggtgacaa gacggccatc aaggtcagca acttcgccta taacctggat     540
cccgacagct tcaagcatgg cgatgtcacc cagtccgacc gccagctggt caagactgtg     600
gtgggctggg cggtcaacga cagcgacacc ccccaatccg gctatgacgt caccctgcgc     660
tacgacacag ccaccaactg gtccaagacc aacacctatg gcctgagcga gaaggtgacc     720
accaagaaca gttcaagtg gccactggtg ggggaaaccc aactctccat cgagattgct     780
gccaatcagt cctgggcgtc ccagaacggg ggctcgacca ccacctcccct gtctcagtcc     840 gtgcgaccga ctgtgccggc ccgctccaag atcccggtga agatagagct ctacaaggcc     900
```

-continued

```
gacatctcct atccctatga gttcaaggcc gatgtcagct atgacctgac cctgagcggc    960
ttcctgcgct ggggcggcaa cgcctggtat acccacccgg acaaccgtcc gaactggaac   1020
cacaccttcg tcataggtcc gtacaaggac aaggcgagca gcattcggta ccagtgggac   1080
aagcgttaca tcccgggtga agtgaagtgg tgggactgga actggaccat acagcagaac   1140
ggtctgtcta ccatgcagaa caacctggcc agagtgctgc cccggtgcg ggcggggatc    1200 accggtgatt tcagtgccga gagccagttt gccggcaaca tagagatcgg tgctcccgtg   1260
ccgctcgcgg ctgacagcca ttcctccaag ctgcagagtg ccgacggcgc tggtcaaggc   1320
ctgaggctgg agatcccgct cgatgcgcaa gagctctccg ggcttggctt caacaacgtc   1380
agcctcagcg tgacccctgc tgccaatcaa                                    1410
```

<210> SEQ ID NO 7
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 7

```
Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
                20                  25                  30

Ser Val Lys Ser Asn Ile Val Gly Met Met Gly Gln Trp Gln Ile Ser
            35                  40                  45

Gly Leu Ala Asn Gly Trp Val Ile Met Gly Pro Gly Tyr Asn Gly Glu
        50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
                100                 105                 110

Ile Lys Pro Thr Ser Tyr Leu Ala His Tyr Leu Gly Tyr Ala Trp Val
            115                 120                 125

Gly Gly Asn His Ser Gln Tyr Val Gly Glu Asp Met Asp Val Thr Arg
        130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
                180                 185                 190

Asp Arg Gln Leu Val Lys Thr Val Val Gly Trp Ala Val Asn Asp Ser
            195                 200                 205

Asp Thr Pro Gln Ser Gly Tyr Asp Val Thr Leu Arg Tyr Asp Thr Ala
        210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
```

-continued

```
              260              265              270
Thr Thr Thr Ser Leu Ser Gln Ser Val Arg Pro Thr Val Pro Ala Arg
         275              280              285
Ser Lys Ile Pro Val Lys Ile Glu Leu Tyr Lys Ala Asp Ile Ser Tyr
     290              295              300
Pro Tyr Glu Phe Lys Ala Asp Val Ser Tyr Asp Leu Thr Leu Ser Gly
305              310              315              320
Phe Leu Arg Trp Gly Gly Asn Ala Trp Tyr Thr His Pro Asp Asn Arg
             325              330              335
Pro Asn Trp Asn His Thr Phe Val Ile Gly Pro Tyr Lys Asp Lys Ala
             340              345              350
Ser Ser Ile Arg Tyr Gln Trp Asp Lys Arg Tyr Ile Pro Gly Glu Val
         355              360              365
Lys Trp Trp Asp Trp Asn Trp Thr Ile Gln Gln Asn Gly Leu Ser Thr
     370              375              380
Met Gln Asn Asn Leu Ala Arg Val Leu Arg Pro Val Arg Ala Gly Ile
385              390              395              400
Thr Gly Asp Phe Ser Ala Glu Ser Gln Phe Ala Gly Asn Ile Glu Ile
             405              410              415
Gly Ala Pro Val Pro Leu Ala Ala Asp Ser His Ser Ser Lys Leu Gln
             420              425              430
Ser Ala Asp Gly Ala Gly Gln Gly Leu Arg Leu Glu Ile Pro Leu Asp
         435              440              445
Ala Gln Glu Leu Ser Gly Leu Gly Phe Asn Asn Val Ser Leu Ser Val
     450              455              460
Thr Pro Ala Ala Asn Gln
465              470
```

```
<210> SEQ ID NO 8
<211> LENGTH: 8
<212> TYPE: PRT
<213> ORGANISM: Artificial Sequence
<220> FEATURE:
<223> OTHER INFORMATION: PSA cleavage site

<400> SEQUENCE: 8

His Ser Ser Lys Leu Gln Ser Ala
1               5

<210> SEQ ID NO 9
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.

<400> SEQUENCE: 9
gcagagcccg tctatccaga ccagcttcgc ttgttttcat tgggccaagg ggtctgtggc      60
gacaagtatc gccccgtcaa tcgagaagaa gcccaaagcg ttaaaagcaa tattgtcggc     120
atgatggggc aatggcaaat aagcgggctg gccaacggct gggtcattat ggggccgggt     180
tataacggtg aaataaaacc agggacagcg tccaatacct ggtgttatcc gaccaatcct     240
gttaccggtg aaataccgac actgtctgcc ctggatattc agatggtga cgaagtcgat     300 gtgcagtggc gactggtaca tgacagtgcg aatttcatca aaccaaccag ctatctggcc     360
cattacctcg gttatgcctg ggtgggcggc aatcacagcc aatatgtcgg cgaagacatg     420
```

-continued

```
gatgtgaccc gtgatggcga cggctgggtg atccgtggca acaatgacgg cggctgtgac      480
ggctatcgct gtggtgacaa gacggccatc aaggtcagca acttcgccta taacctggat      540
cccgacagct tcaagcatgg cgatgtcacc cagtccgacc gccagctggt caagactgtg      600
gtgggctggg cggtcaacga cagcgacacc ccccaatccg gctatgacgt caccctgcgc      660
tacgacacag ccaccaactg gtccaagacc aacacctatg cctgagcga gaaggtgacc      720 accaagaaca agttcaagtg gccactggtg ggggaaaccc aactctccat cgagattgct      780
gccaatcagt cctgggcgtc ccagaacggg ggctcgacca ccacctccct gtctcagtcc      840
gtgcgaccga ctgtgccggc ccgctccaag atcccggtga agatagagct ctacaaggcc      900
gacatctcct atccctatga gttcaaggcc gatgtcagct atgacctgac cctgagcggc      960
ttcctgcgct ggggcggcaa cgcctggtat acccacccgg acaaccgtcc gaactggaac      1020
cacaccttcg tcataggtcc gtacaaggac aaggcgagca gcattcggta ccagtgggac      1080
aagcgttaca tcccgggtga agtgaagtgg tgggactgga actggaccat acagcagaac      1140
ggtctgtcta ccatgcagaa caacctggcc agagtgctgc gcccggtgcg ggcggggatc      1200
accggtgatt tcagtgccga gagccagttt gccggcaaca tagagatcgg tgctcccgtg      1260
ccgctcgcgg ctgactccca gttctatagc agcaatagtg tggacggcgc tggtcaaggc      1320
ctgaggctgg agatcccgct cgatgcgcaa gagctctccg ggcttggctt caacaacgtc      1380
agcctcagcg tgacccctgc tgccaatcaa                                       1410
```

```
<210> SEQ ID NO 10
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 10

Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
            100                 105                 110

Ile Lys Pro Thr Ser Tyr Leu Ala His Tyr Leu Gly Tyr Ala Trp Val
        115                 120                 125

Gly Gly Asn His Ser Gln Tyr Val Gly Glu Asp Met Asp Val Thr Arg
    130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
```

```
                180             185             190

Asp Arg Gln Leu Val Lys Thr Val Val Gly Trp Ala Val Asn Asp Ser
            195             200             205

Asp Thr Pro Gln Ser Gly Tyr Asp Val Thr Leu Arg Tyr Asp Thr Ala
    210             215             220

Thr Asn Trp Ser Lys Thr Asn Thr Tyr Gly Leu Ser Glu Lys Val Thr
225             230             235             240

Thr Lys Asn Lys Phe Lys Trp Pro Leu Val Gly Glu Thr Gln Leu Ser
            245             250             255

Ile Glu Ile Ala Ala Asn Gln Ser Trp Ala Ser Gln Asn Gly Gly Ser
            260             265             270

Thr Thr Thr Ser Leu Ser Gln Ser Val Arg Pro Thr Val Pro Ala Arg
        275             280             285

Ser Lys Ile Pro Val Lys Ile Glu Leu Tyr Lys Ala Asp Ile Ser Tyr
    290             295             300

Pro Tyr Glu Phe Lys Ala Asp Val Ser Tyr Asp Leu Thr Leu Ser Gly
305             310             315             320

Phe Leu Arg Trp Gly Gly Asn Ala Trp Tyr Thr His Pro Asp Asn Arg
            325             330             335

Pro Asn Trp Asn His Thr Phe Val Ile Gly Pro Tyr Lys Asp Lys Ala
            340             345             350

Ser Ser Ile Arg Tyr Gln Trp Asp Lys Arg Tyr Ile Pro Gly Glu Val
            355             360             365

Lys Trp Trp Asp Trp Asn Trp Thr Ile Gln Gln Asn Gly Leu Ser Thr
    370             375             380

Met Gln Asn Asn Leu Ala Arg Val Leu Arg Pro Val Arg Ala Gly Ile
385             390             395             400

Thr Gly Asp Phe Ser Ala Glu Ser Gln Phe Ala Gly Asn Ile Glu Ile
            405             410             415

Gly Ala Pro Val Pro Leu Ala Ala Asp Ser Gln Phe Tyr Ser Ser Asn
            420             425             430

Ser Val Asp Gly Ala Gly Gln Gly Leu Arg Leu Glu Ile Pro Leu Asp
        435             440             445

Ala Gln Glu Leu Ser Gly Leu Gly Phe Asn Asn Val Ser Leu Ser Val
    450             455             460

Thr Pro Ala Ala Asn Gln
465             470
```

```
<210> SEQ ID NO 11
<211> LENGTH: 6
<212> TYPE: PRT
<213> ORGANISM: Artificial Sequence
<220> FEATURE:
<223> OTHER INFORMATION: PSA cleavage site

<400> SEQUENCE: 11

Gln Phe Tyr Ser Ser Asn
1               5

<210> SEQ ID NO 12
<211> LENGTH: 1410
<212> TYPE: DNA
<213> ORGANISM: Artificial Sequence
<220> FEATURE:
<223> OTHER INFORMATION: Proaerolysin with a PSA sequence substituted
      for the furin site.

<400> SEQUENCE: 12
```

-continued

```
gcagagcccg tctatccaga ccagcttcgc ttgtttttcat tgggccaagg ggtctgtggc      60
gacaagtatc gccccgtcaa tcgagaagaa gcccaaagcg ttaaaagcaa tattgtcggc     120
atgatggggc aatggcaaat aagcgggctg gccaacggct gggtcattat ggggccgggt     180
tataacggtg aaataaaacc agggacagcg tccaatacct ggtgttatcc gaccaatcct     240
gttaccggtg aaataccgac actgtctgcc ctggatattc agatggtgac gaagtcgat      300 gtgcagtggc gactggtaca tgacagtgcg aatttcatca aaccaaccag ctatctggcc     360
cattacctcg gttatgcctg ggtgggcggc aatcacagcc aatatgtcgg cgaagacatg     420 gatgtgacc  gtgatggcga cggctgggtg atccgtggca caatgacgg  cggctgtgac     480 ggctatcgct gtggtgacaa gacggccatc aaggtcagca acttcgccta taacctggat     540
cccgacagct tcaagcatgg cgatgtcacc cagtccgacc gccagctggt caagactgtg     600
gtgggctggg cggtcaacga cagcgacacc ccccaatccg gctatgacgt caccctgcgc     660
tacgacacag ccaccaactg gtccaagacc aacacctatg cctgagcga  gaaggtgacc     720 accaagaaca agttcaagtg gccactggtg ggggaaaccc aactctccat cgagattgct     780
gccaatcagt cctgggcgtc ccagaacggg ggctcgacca ccacctccct gtctcagtcc     840
gtgcgaccga ctgtgccggc ccgctccaag atcccggtga agatagagct ctacaaggcc     900
gacatctcct atccctatga gttcaaggcc gatgtcagct atgacctgac cctgagcggc     960
ttcctgcgct ggggcggcaa cgcctggtat acccacccgg acaaccgtcc gaactggaac    1020
cacaccttcg tcataggtcc gtacaaggac aaggcgagca gcattcggta ccagtgggac    1080
aagcgttaca tcccgggtga agtgaagtgg tgggactgga actggaccat acagcagaac    1140
ggtctgtcta ccatgcagaa caacctggcc agagtgctgc gcccggtgcg ggcggggatc    1200
accggtgatt tcagtgccga gagccagttt gccggcaaca tagagatcgg tgctcccgtg    1260
ccgctcgcgg ctgacggtat aagtagtttc cagagtagtg tggacggcgc tggtcaaggc    1320
ctgaggctgg agatcccgct cgatgcgcaa gagctctccg ggcttggctt caacaacgtc    1380
agcctcagcg tgacccctgc tgccaatcaa                                     1410
```

<210> SEQ ID NO 13
<211> LENGTH: 470
<212> TYPE: PRT
<213> ORGANISM: Artificial Sequence
<220> FEATURE:
<223> OTHER INFORMATION: Proaerolysin with a PSA sequence substituted
      for the furin site.

<400> SEQUENCE: 13

```
Ala Glu Pro Val Tyr Pro Asp Gln Leu Arg Leu Phe Ser Leu Gly Gln
1               5                   10                  15

Gly Val Cys Gly Asp Lys Tyr Arg Pro Val Asn Arg Glu Glu Ala Gln
            20                  25                  30

Ser Val Lys Ser Asn Ile Val Gly Met Met Gly Gln Trp Gln Ile Ser
        35                  40                  45

Gly Leu Ala Asn Gly Trp Val Ile Met Gly Pro Gly Tyr Asn Gly Glu
    50                  55                  60

Ile Lys Pro Gly Thr Ala Ser Asn Thr Trp Cys Tyr Pro Thr Asn Pro
65                  70                  75                  80

Val Thr Gly Glu Ile Pro Thr Leu Ser Ala Leu Asp Ile Pro Asp Gly
                85                  90                  95

Asp Glu Val Asp Val Gln Trp Arg Leu Val His Asp Ser Ala Asn Phe
```

-continued

```
                100                 105                 110

Ile Lys Pro Thr Ser Tyr Leu Ala His Tyr Leu Gly Tyr Ala Trp Val
            115                 120                 125

Gly Gly Asn His Ser Gln Tyr Val Gly Glu Asp Met Asp Val Thr Arg
        130                 135                 140

Asp Gly Asp Gly Trp Val Ile Arg Gly Asn Asn Asp Gly Gly Cys Asp
145                 150                 155                 160

Gly Tyr Arg Cys Gly Asp Lys Thr Ala Ile Lys Val Ser Asn Phe Ala
                165                 170                 175

Tyr Asn Leu Asp Pro Asp Ser Phe Lys His Gly Asp Val Thr Gln Ser
            180                 185                 190

Asp Arg Gln Leu Val Lys Thr Val Val Gly Trp Ala Val Asn Asp Ser
        195                 200                 205

Asp Thr Pro Gln Ser Gly Tyr Asp Val Thr Leu Arg Tyr Asp Thr Ala
        210                 215                 220

Thr Asn Trp Ser Lys Thr Asn Thr Tyr Gly Leu Ser Glu Lys Val Thr
225                 230                 235                 240

Thr Lys Asn Lys Phe Lys Trp Pro Leu Val Gly Glu Thr Gln Leu Ser
                245                 250                 255

Ile Glu Ile Ala Ala Asn Gln Ser Trp Ala Ser Gln Asn Gly Gly Ser
            260                 265                 270

Thr Thr Thr Ser Leu Ser Gln Ser Val Arg Pro Thr Val Pro Ala Arg
            275                 280                 285

Ser Lys Ile Pro Val Lys Ile Glu Leu Tyr Lys Ala Asp Ile Ser Tyr
        290                 295                 300

Pro Tyr Glu Phe Lys Ala Asp Val Ser Tyr Asp Leu Thr Leu Ser Gly
305                 310                 315                 320

Phe Leu Arg Trp Gly Gly Asn Ala Trp Tyr Thr His Pro Asp Asn Arg
                325                 330                 335

Pro Asn Trp Asn His Thr Phe Val Ile Gly Pro Tyr Lys Asp Lys Ala
            340                 345                 350

Ser Ser Ile Arg Tyr Gln Trp Asp Lys Arg Tyr Ile Pro Gly Glu Val
            355                 360                 365

Lys Trp Trp Asp Trp Asn Trp Thr Ile Gln Gln Asn Gly Leu Ser Thr
        370                 375                 380

Met Gln Asn Asn Leu Ala Arg Val Leu Arg Pro Val Arg Ala Gly Ile
385                 390                 395                 400

Thr Gly Asp Phe Ser Ala Glu Ser Gln Phe Ala Gly Asn Ile Glu Ile
                405                 410                 415

Gly Ala Pro Val Pro Leu Ala Ala Asp Gly Ile Ser Ser Phe Gln Ser
            420                 425                 430

Ser Val Asp Gly Ala Gly Gln Gly Leu Arg Leu Glu Ile Pro Leu Asp
            435                 440                 445

Ala Gln Glu Leu Ser Gly Leu Gly Phe Asn Asn Val Ser Leu Ser Val
        450                 455                 460

Thr Pro Ala Ala Asn Gln
465                 470
```

<210> SEQ ID NO 14
<211> LENGTH: 7
<212> TYPE: PRT
<213> ORGANISM: Artificial Sequence
<220> FEATURE:
<223> OTHER INFORMATION: PSA cleavage site

```
<400> SEQUENCE: 14

Gly Ile Ser Ser Phe Gln Ser
1               5

<210> SEQ ID NO 15
<211> LENGTH: 7
<212> TYPE: PRT
<213> ORGANISM: Homo sapiens

<400> SEQUENCE: 15

Lys Gly Ile Ser Ser Gln Tyr
1               5

<210> SEQ ID NO 16
<211> LENGTH: 7
<212> TYPE: PRT
<213> ORGANISM: Homo sapiens

<400> SEQUENCE: 16

Ser Arg Lys Ser Gln Gln Tyr
1               5

<210> SEQ ID NO 17
<211> LENGTH: 7
<212> TYPE: PRT
<213> ORGANISM: Homo sapiens

<400> SEQUENCE: 17

Ala Thr Lys Ser Lys Gln His
1               5

<210> SEQ ID NO 18
<211> LENGTH: 7
<212> TYPE: PRT
<213> ORGANISM: Homo sapiens

<400> SEQUENCE: 18

Lys Gly Leu Ser Ser Gln Cys
1               5

<210> SEQ ID NO 19
<211> LENGTH: 7
<212> TYPE: PRT
<213> ORGANISM: Homo sapiens

<400> SEQUENCE: 19

Leu Gly Gly Ser Ser Gln Leu
1               5

<210> SEQ ID NO 20
<211> LENGTH: 7
<212> TYPE: PRT
<213> ORGANISM: Homo sapiens

<400> SEQUENCE: 20

Glu His Ser Ser Lys Leu Gln
1               5

<210> SEQ ID NO 21
<211> LENGTH: 4
<212> TYPE: PRT
<213> ORGANISM: Homo sapiens

<400> SEQUENCE: 21
```

-continued

```
Ser Lys Leu Gln
1

<210> SEQ ID NO 22
<211> LENGTH: 10
<212> TYPE: PRT
<213> ORGANISM: Artificial sequence
<220> FEATURE:
<223> OTHER INFORMATION: LHRH variant sequence

<400> SEQUENCE: 22

Gln His Trp Ser Tyr Gly Leu Arg Pro Gly
1               5               10

<210> SEQ ID NO 23
<211> LENGTH: 10
<212> TYPE: PRT
<213> ORGANISM: Artificial Sequence
<220> FEATURE:
<223> OTHER INFORMATION: LHRH variant sequence

<400> SEQUENCE: 23

Glu His Trp Ser Tyr Lys Leu Arg Pro Gly
1               5               10

<210> SEQ ID NO 24
<211> LENGTH: 397
<212> TYPE: PRT
<213> ORGANISM: Artificial Sequence
<220> FEATURE:
<223> OTHER INFORMATION: Variant proaerolysin peptide

<400> SEQUENCE: 24

Glu His Trp Ser Tyr Lys Leu Arg Pro Gly Glu Ile Pro Thr Leu Ser
1               5               10              15

Ala Leu Asp Ile Pro Asp Gly Asp Glu Val Asp Val Gln Trp Arg Leu
            20              25              30

Val His Asp Ser Ala Asn Phe Ile Lys Pro Thr Ser Tyr Leu Ala His
        35              40              45

Tyr Leu Gly Tyr Ala Trp Val Gly Gly Asn His Ser Gln Tyr Val Gly
    50              55              60

Glu Asp Met Asp Val Thr Arg Asp Gly Asp Gly Trp Val Ile Arg Gly
65              70              75              80

Asn Asn Asp Gly Gly Cys Asp Gly Tyr Arg Cys Gly Asp Lys Thr Ala
            85              90              95

Ile Lys Val Ser Asn Phe Ala Tyr Asn Leu Asp Pro Asp Ser Phe Lys
            100             105             110

His Gly Asp Val Thr Gln Ser Asp Arg Gln Leu Val Lys Thr Val Val
        115             120             125

Gly Trp Ala Val Asn Asp Ser Asp Thr Pro Gln Ser Gly Tyr Asp Val
        130             135             140

Thr Leu Arg Tyr Asp Thr Ala Thr Asn Trp Ser Lys Thr Asn Thr Tyr
145             150             155             160

Gly Leu Ser Glu Lys Val Thr Thr Lys Asn Lys Phe Lys Trp Pro Leu
            165             170             175

Val Gly Glu Thr Gln Leu Ser Ile Glu Ile Ala Ala Asn Gln Ser Trp
            180             185             190

Ala Ser Gln Asn Gly Gly Ser Thr Thr Thr Ser Leu Ser Gln Ser Val
        195             200             205

Arg Pro Thr Val Pro Ala Arg Ser Lys Ile Pro Val Lys Ile Glu Leu
```

-continued

```
        210               215               220
Tyr Lys Ala Asp Ile Ser Tyr Pro Tyr Glu Phe Lys Ala Asp Val Ser
225               230               235               240

Tyr Asp Leu Thr Leu Ser Gly Phe Leu Arg Trp Gly Gly Asn Ala Trp
                245               250               255

Tyr Thr His Pro Asp Asn Arg Pro Asn Trp Asn His Thr Phe Val Ile
            260               265               270

Gly Pro Tyr Lys Asp Lys Ala Ser Ser Ile Arg Tyr Gln Trp Asp Lys
            275               280               285

Arg Tyr Ile Pro Gly Glu Val Lys Trp Trp Asp Trp Asn Trp Thr Ile
        290               295               300

Gln Gln Asn Gly Leu Ser Thr Met Gln Asn Asn Leu Ala Arg Val Leu
305               310               315               320

Arg Pro Val Arg Ala Gly Ile Thr Gly Asp Phe Ser Ala Glu Ser Gln
                325               330               335

Phe Ala Gly Asn Ile Glu Ile Gly Ala Pro Val Pro Leu Ala Ala Asp
                340               345               350

Ser His Ser Ser Lys Leu Gln Ser Val Asp Gly Ala Gly Gln Gly Leu
            355               360               365

Arg Leu Glu Ile Pro Leu Asp Ala Gln Glu Leu Ser Gly Leu Gly Phe
        370               375               380

Asn Asn Val Ser Leu Ser Val Thr Pro Ala Ala Asn Gln
385               390               395
```

```
<210> SEQ ID NO 25
<211> LENGTH: 397
<212> TYPE: PRT
<213> ORGANISM: Artificial Sequence
<220> FEATURE:
<223> OTHER INFORMATION: Variant proaerolysin peptide

<400> SEQUENCE: 25

Glu His Trp Ser Tyr Lys Leu Arg Pro Gly Glu Ile Pro Thr Leu Ser
1               5               10               15

Ala Leu Asp Ile Pro Asp Gly Asp Glu Val Asp Val Gln Trp Arg Leu
                20               25               30

Val His Asp Ser Ala Asn Phe Ile Lys Pro Thr Ser Tyr Leu Ala His
            35               40               45

Tyr Leu Gly Tyr Ala Trp Val Gly Gly Asn His Ser Gln Tyr Val Gly
        50               55               60

Glu Asp Met Asp Val Thr Arg Asp Gly Asp Gly Trp Val Ile Arg Gly
65               70               75               80

Asn Asn Asp Gly Gly Cys Asp Gly Tyr Arg Cys Gly Asp Lys Thr Ala
                85               90               95

Ile Lys Val Ser Asn Phe Ala Tyr Asn Leu Asp Pro Asp Ser Phe Lys
                100               105               110

His Gly Asp Val Thr Gln Ser Asp Arg Gln Leu Val Lys Thr Val Val
            115               120               125

Gly Trp Ala Val Asn Asp Ser Asp Thr Pro Gln Ser Gly Tyr Asp Val
        130               135               140

Thr Leu Arg Tyr Asp Thr Ala Thr Asn Trp Ser Lys Thr Asn Thr Tyr
145               150               155               160

Gly Leu Ser Glu Lys Val Thr Thr Lys Asn Lys Phe Lys Trp Pro Leu
                165               170               175

Val Gly Glu Thr Gln Leu Ser Ile Glu Ile Ala Ala Asn Gln Ser Trp
```

-continued

```
                180                   185                   190
Ala Ser Gln Asn Gly Gly Ser Thr Thr Thr Ser Leu Ser Gln Ser Val
        195                   200                   205

Arg Pro Thr Val Pro Ala Arg Ser Lys Ile Pro Val Lys Ile Glu Leu
    210                   215                   220

Tyr Lys Ala Asp Ile Ser Tyr Pro Tyr Glu Phe Lys Ala Asp Val Ser
225                   230                   235                   240

Tyr Asp Leu Thr Leu Ser Gly Phe Leu Arg Trp Gly Gly Asn Ala Trp
                245                   250                   255

Tyr Thr His Pro Asp Asn Arg Pro Asn Trp Asn His Thr Phe Val Ile
                260                   265                   270

Gly Pro Tyr Lys Asp Lys Ala Ser Ser Ile Arg Tyr Gln Trp Asp Lys
                275                   280                   285

Arg Tyr Ile Pro Gly Glu Val Lys Trp Trp Asp Trp Asn Trp Thr Ile
    290                   295                   300

Gln Gln Asn Gly Leu Ser Thr Met Gln Asn Asn Leu Ala Arg Val Leu
305                   310                   315                   320

Arg Pro Val Arg Ala Gly Ile Thr Gly Asp Phe Ser Ala Glu Ser Gln
                325                   330                   335

Phe Ala Gly Asn Ile Glu Ile Gly Ala Pro Val Pro Leu Ala Ala Asp
                340                   345                   350

Ser Lys Val Arg Arg Ala Arg Ser Val Asp Gly Ala Gly Gln Gly Leu
                355                   360                   365

Arg Leu Glu Ile Pro Leu Asp Ala Gln Glu Leu Ser Gly Leu Gly Phe
    370                   375                   380

Asn Asn Val Ser Leu Ser Val Thr Pro Ala Ala Asn Gln
385                   390                   395
```

<210> SEQ ID NO 26
<211> LENGTH: 476
<212> TYPE: PRT
<213> ORGANISM: Artificial Sequence
<220> FEATURE:
<223> OTHER INFORMATION: Proaerolysin with PSA sequence substituted for
      the furin site and an N-terminal His tag.

<400> SEQUENCE: 26

```
His His His His His His Ala Glu Pro Val Tyr Pro Asp Gln Leu Arg
1               5                   10                  15

Leu Phe Ser Leu Gly Gln Gly Val Cys Gly Asp Lys Tyr Arg Pro Val
        20                  25                  30

Asn Arg Glu Glu Ala Gln Ser Val Lys Ser Asn Ile Val Gly Met Met
        35                  40                  45

Gly Gln Trp Gln Ile Ser Gly Leu Ala Asn Gly Trp Val Ile Met Gly
    50                  55                  60

Pro Gly Tyr Asn Gly Glu Ile Lys Pro Gly Thr Ala Ser Asn Thr Trp
65                  70                  75                  80

Cys Tyr Pro Thr Asn Pro Val Thr Gly Glu Ile Pro Thr Leu Ser Ala
                85                  90                  95

Leu Asp Ile Pro Asp Gly Asp Glu Val Asp Val Gln Trp Arg Leu Val
            100                 105                 110

His Asp Ser Ala Asn Phe Ile Lys Pro Thr Ser Tyr Leu Ala His Tyr
        115                 120                 125

Leu Gly Tyr Ala Trp Val Gly Gly Asn His Ser Gln Tyr Val Gly Glu
    130                 135                 140
```

-continued

```
Asp Met Asp Val Thr Arg Asp Gly Asp Gly Trp Val Ile Arg Gly Asn
145                 150                 155                 160

Asn Asp Gly Gly Cys Asp Gly Tyr Arg Cys Gly Asp Lys Thr Ala Ile
                165                 170                 175

Lys Val Ser Asn Phe Ala Tyr Asn Leu Asp Pro Asp Ser Phe Lys His
                180                 185                 190

Gly Asp Val Thr Gln Ser Asp Arg Gln Leu Val Lys Thr Val Val Gly
                195                 200                 205

Trp Ala Val Asn Asp Ser Asp Thr Pro Gln Ser Gly Tyr Asp Val Thr
        210                 215                 220

Leu Arg Tyr Asp Thr Ala Thr Asn Trp Ser Lys Thr Asn Thr Tyr Gly
225                 230                 235                 240

Leu Ser Glu Lys Val Thr Thr Lys Asn Lys Phe Lys Trp Pro Leu Val
                245                 250                 255

Gly Glu Thr Gln Leu Ser Ile Glu Ile Ala Ala Asn Gln Ser Trp Ala
                260                 265                 270

Ser Gln Asn Gly Gly Ser Thr Thr Thr Ser Leu Ser Gln Ser Val Arg
                275                 280                 285

Pro Thr Val Pro Ala Arg Ser Lys Ile Pro Val Lys Ile Glu Leu Tyr
        290                 295                 300

Lys Ala Asp Ile Ser Tyr Pro Tyr Glu Phe Lys Ala Asp Val Ser Tyr
305                 310                 315                 320

Asp Leu Thr Leu Ser Gly Phe Leu Arg Trp Gly Gly Asn Ala Trp Tyr
                325                 330                 335

Thr His Pro Asp Asn Arg Pro Asn Trp Asn His Thr Phe Val Ile Gly
                340                 345                 350

Pro Tyr Lys Asp Lys Ala Ser Ser Ile Arg Tyr Gln Trp Asp Lys Arg
                355                 360                 365

Tyr Ile Pro Gly Glu Val Lys Trp Trp Asp Trp Asn Trp Thr Ile Gln
        370                 375                 380

Gln Asn Gly Leu Ser Thr Met Gln Asn Asn Leu Ala Arg Val Leu Arg
385                 390                 395                 400

Pro Val Arg Ala Gly Ile Thr Gly Asp Phe Ser Ala Glu Ser Gln Phe
                405                 410                 415

Ala Gly Asn Ile Glu Ile Gly Ala Pro Val Pro Leu Ala Ala Asp Ser
                420                 425                 430

His Ser Ser Lys Leu Gln Ser Val Asp Gly Ala Gly Gln Gly Leu Arg
                435                 440                 445

Leu Glu Ile Pro Leu Asp Ala Gln Glu Leu Ser Gly Leu Gly Phe Asn
        450                 455                 460

Asn Val Ser Leu Ser Val Thr Pro Ala Ala Asn Gln
465                 470                 475
```

```
<210> SEQ ID NO 27
<211> LENGTH: 585
<212> TYPE: PRT
<213> ORGANISM: Homo sapiens
<220> FEATURE:
<221> NAME/KEY: MISC_FEATURE
<222> LOCATION: (1)..(585)
<223> OTHER INFORMATION: Human Albumin mature sequence

<400> SEQUENCE: 27

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
```

-continued

```
                  20                  25                  30

Gln Cys Pro Phe Glu Asp His Val Lys Leu Val Asn Glu Val Thr Glu
             35                  40                  45

Phe Ala Lys Thr Cys Val Ala Asp Glu Ser Ala Glu Asn Cys Asp Lys
         50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                 85                  90                  95

Glu Arg Asn Glu Cys Phe Leu Gln His Lys Asp Asp Asn Pro Asn Leu
             100                 105                 110

Pro Arg Leu Val Arg Pro Glu Val Asp Val Met Cys Thr Ala Phe His
         115                 120                 125

Asp Asn Glu Glu Thr Phe Leu Lys Lys Tyr Leu Tyr Glu Ile Ala Arg
         130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                 165                 170                 175

Cys Leu Leu Pro Lys Leu Asp Glu Leu Arg Asp Glu Gly Lys Ala Ser
             180                 185                 190

Ser Ala Lys Gln Arg Leu Lys Cys Ala Ser Leu Gln Lys Phe Gly Glu
             195                 200                 205

Arg Ala Phe Lys Ala Trp Ala Val Ala Arg Leu Ser Gln Arg Phe Pro
         210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                 245                 250                 255

Arg Ala Asp Leu Ala Lys Tyr Ile Cys Glu Asn Gln Asp Ser Ile Ser
             260                 265                 270

Ser Lys Leu Lys Glu Cys Cys Glu Lys Pro Leu Leu Glu Lys Ser His
             275                 280                 285

Cys Ile Ala Glu Val Glu Asn Asp Glu Met Arg Ala Asp Leu Pro Ser
         290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
             325                 330                 335

Arg His Pro Asp Tyr Ser Val Val Leu Leu Leu Arg Leu Ala Lys Thr
             340                 345                 350

Tyr Glu Thr Thr Leu Glu Lys Cys Cys Ala Ala Ala Asp Pro His Glu
             355                 360                 365

Cys Tyr Ala Lys Val Phe Asp Glu Phe Lys Pro Leu Val Glu Glu Pro
         370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
             405                 410                 415

Gln Val Ser Thr Pro Thr Leu Val Glu Val Ser Arg Asn Leu Gly Lys
             420                 425                 430

Val Gly Ser Lys Cys Cys Lys His Pro Glu Ala Lys Arg Met Pro Cys
             435                 440                 445
```

-continued

```
Ala Glu Asp Tyr Leu Ser Val Val Leu Asn Gln Leu Cys Val Leu His
    450             455             460
```

```
Glu Lys Thr Pro Val Ser Asp Arg Val Thr Lys Cys Cys Thr Glu Ser
465             470             475             480
```

```
Leu Val Asn Arg Arg Pro Cys Phe Ser Ala Leu Glu Val Asp Glu Thr
                485             490             495
```

```
Tyr Val Pro Lys Glu Phe Asn Ala Glu Thr Phe Thr Phe His Ala Asp
                500             505             510
```

```
Ile Cys Thr Leu Ser Glu Lys Glu Arg Gln Ile Lys Lys Gln Thr Ala
            515             520             525
```

```
Leu Val Glu Leu Val Lys His Lys Pro Lys Ala Thr Lys Glu Gln Leu
    530             535             540
```

```
Lys Ala Val Met Asp Asp Phe Ala Ala Phe Val Glu Lys Cys Cys Lys
545             550             555             560
```

```
Ala Asp Asp Lys Glu Thr Cys Phe Ala Glu Glu Gly Lys Lys Leu Val
                565             570             575
```

```
Ala Ala Ser Gln Ala Ala Leu Gly Leu
            580             585
```

```
<210> SEQ ID NO 28
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 28

Gln Lys Arg Arg
1

<210> SEQ ID NO 29
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 29

Lys Ser Arg Arg
1

<210> SEQ ID NO 30
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 30

Ala Lys Arg Arg
1

<210> SEQ ID NO 31
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 31

Lys Lys Arg Arg
1
```

```
<210> SEQ ID NO 32
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 32

His Lys Arg Arg
1

<210> SEQ ID NO 33
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 33

Lys Ala Phe Arg
1

<210> SEQ ID NO 34
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 34

Lys Ala Gln Arg
1

<210> SEQ ID NO 35
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 35

Lys Ala Lys Arg
1

<210> SEQ ID NO 36
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 36

Lys Ala Arg Lys
1

<210> SEQ ID NO 37
<211> LENGTH: 4
<212> TYPE: PRT
<213> ORGANISM: Artificial Sequence
<220> FEATURE:
<223> OTHER INFORMATION: HK2-specific cleavage site

<400> SEQUENCE: 37

Lys Ala His Arg
1
```

-continued

```
<210> SEQ ID NO 38
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 38

His Ala Gln Lys Arg Arg
1               5

<210> SEQ ID NO 39
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 39

Gly Gly Lys Ser Arg Arg
1               5

<210> SEQ ID NO 40
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 40

His Glu Gln Lys Arg Arg
1               5

<210> SEQ ID NO 41
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 41

His Glu Ala Lys Arg Arg
1               5

<210> SEQ ID NO 42
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 42

Gly Gly Gln Lys Arg Arg
1               5

<210> SEQ ID NO 43
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 43

His Glu Gln Lys Arg Arg
1               5
```

```
<210> SEQ ID NO 44
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 44

Gly Gly Ala Lys Arg Arg
1               5

<210> SEQ ID NO 45
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 45

His Glu Gln Lys Arg Arg
1               5

<210> SEQ ID NO 46
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 46

Gly Gly Lys Lys Arg Arg
1               5

<210> SEQ ID NO 47
<211> LENGTH: 6
<212> TYPE: PRT
<213> ORGANISM: Artificial Sequence
<220> FEATURE:
<223> OTHER INFORMATION: HK2-specific cleavage site

<400> SEQUENCE: 47

Gly Gly His Lys Arg Arg
1               5

<210> SEQ ID NO 48
<211> LENGTH: 1061
<212> TYPE: PRT
<213> ORGANISM: Artificial Sequence
<220> FEATURE:
<223> OTHER INFORMATION: HSA fused to PRC302 with one PSA cleavage site
      linker

<400> SEQUENCE: 48

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95
```

```
Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
            115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Arg Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510
```

-continued

```
Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu His Ser Ser Lys Leu Gln Ala
                580                 585                 590

Glu Pro Val Tyr Pro Asp Gln Leu Arg Leu Phe Ser Leu Gly Gln Gly
                595                 600                 605

Val Cys Gly Asp Lys Tyr Arg Pro Val Asn Arg Glu Glu Ala Gln Ser
        610                 615                 620

Val Lys Ser Asn Ile Val Gly Met Met Gly Gln Trp Gln Ile Ser Gly
625                 630                 635                 640

Leu Ala Asn Gly Trp Val Ile Met Gly Pro Gly Tyr Asn Gly Glu Ile
                645                 650                 655

Lys Pro Gly Thr Ala Ser Asn Thr Trp Cys Tyr Pro Thr Asn Pro Val
                660                 665                 670

Thr Gly Glu Ile Pro Thr Leu Ser Ala Leu Asp Ile Pro Asp Gly Asp
        675                 680                 685

Glu Val Asp Val Gln Trp Arg Leu Val His Asp Ser Ala Asn Phe Ile
        690                 695                 700

Lys Pro Thr Ser Tyr Leu Ala His Tyr Leu Gly Tyr Ala Trp Val Gly
705                 710                 715                 720

Gly Asn His Ser Gln Tyr Val Gly Glu Asp Met Asp Val Thr Arg Asp
                725                 730                 735

Gly Asp Gly Trp Val Ile Arg Gly Asn Asn Asp Gly Gly Cys Asp Gly
                740                 745                 750

Tyr Arg Cys Gly Asp Lys Thr Ala Ile Lys Val Ser Asn Phe Ala Tyr
        755                 760                 765

Asn Leu Asp Pro Asp Ser Phe Lys His Gly Asp Val Thr Gln Ser Asp
        770                 775                 780

Arg Gln Leu Val Lys Thr Val Val Gly Trp Ala Val Asn Asp Ser Asp
785                 790                 795                 800

Thr Pro Gln Ser Gly Tyr Asp Val Thr Leu Arg Tyr Asp Thr Ala Thr
                805                 810                 815

Asn Trp Ser Lys Thr Asn Thr Tyr Gly Leu Ser Glu Lys Val Thr Thr
                820                 825                 830

Lys Asn Lys Phe Lys Trp Pro Leu Val Gly Glu Thr Gln Leu Ser Ile
        835                 840                 845

Glu Ile Ala Ala Asn Gln Ser Trp Ala Ser Gln Asn Gly Gly Ser Thr
        850                 855                 860

Thr Thr Ser Leu Ser Gln Ser Val Arg Pro Thr Val Pro Ala Arg Ser
865                 870                 875                 880

Lys Ile Pro Val Lys Ile Glu Leu Tyr Lys Ala Asp Ile Ser Tyr Pro
                885                 890                 895

Tyr Glu Phe Lys Ala Asp Val Ser Tyr Asp Leu Thr Leu Ser Gly Phe
                900                 905                 910

Leu Arg Trp Gly Gly Asn Ala Trp Tyr Thr His Pro Asp Asn Arg Pro
        915                 920                 925

Asn Trp Asn His Thr Phe Val Ile Gly Pro Tyr Lys Asp Lys Ala Ser
```

-continued

```
      930                935                940

Ser Ile Arg Tyr Gln Trp Asp Lys Arg Tyr Ile Pro Gly Glu Val Lys
945                950                955                960

Trp Trp Asp Trp Asn Trp Thr Ile Gln Gln Asn Gly Leu Ser Thr Met
                 965                970                975

Gln Asn Asn Leu Ala Arg Val Leu Arg Pro Val Arg Ala Gly Ile Thr
             980                985                990

Gly Asp Phe Ser Ala Glu Ser Gln  Phe Ala Gly Asn Ile  Glu Ile Gly
        995                1000                1005

Ala Pro  Val Pro Leu Ala Ala  Asp Ser His Ser Ser  Lys Leu Gln
    1010                1015                1020

Ser Val  Asp Gly Ala Gly Gln  Gly Leu Arg Leu Glu  Ile Pro Leu
    1025                1030                1035

Asp Ala  Gln Glu Leu Ser Gly  Leu Gly Phe Asn Asn  Val Ser Leu
    1040                1045                1050

Ser Val  Thr Pro Ala Ala Asn  Gln
    1055                1060
```